United States Patent [19]
Brichard et al.

[11] Patent Number: 6,096,520
[45] Date of Patent: Aug. 1, 2000

[54] BRAIN GLYCOGEN PHOSPHORYLASE CANCER ANTIGEN

[75] Inventors: Vincent Brichard; Aline van Pel; Thierry Boon-Falleur, all of Brussels, Belgium; Fredric A. Gorin, Davis, Calif.

[73] Assignees: Ludwig Institute for Cancer Research, New York, N.Y.; The Regents of the University of California, Oakland, Calif.

[21] Appl. No.: 09/215,966

[22] Filed: Dec. 18, 1998

Related U.S. Application Data

[63] Continuation of application No. 08/672,351, Jun. 25, 1996, abandoned.

[51] Int. Cl.[7] .......................... C12N 15/54; C12N 15/09; C12N 15/63; C07K 7/00; C07K 14/435
[52] U.S. Cl. .................. 435/69.3; 435/69.7; 435/194; 435/320.1; 435/325; 536/23.2; 536/23.4; 536/23.5; 530/324; 530/325; 530/326; 530/327; 530/328; 530/329
[58] Field of Search ................... 435/69.1, 69.7, 435/69.3, 194, 320.1, 325; 530/350, 324, 325, 326, 327, 328, 329; 536/23.5, 23.2, 23.4

[56] References Cited

U.S. PATENT DOCUMENTS 5,342,774  8/1994  Boon et al. .
5,405,940  4/1995  Boon et al. .

FOREIGN PATENT DOCUMENTS

WO92/20356  11/1992  WIPO .
WO9601557   5/1993   WIPO .
WO9414459   7/1994   WIPO .
WO94/21126  9/1994   WIPO .
WO95/00159  1/1995   WIPO .
WO95/03422  2/1995   WIPO .
WO96/01557  1/1996   WIPO .

OTHER PUBLICATIONS

Traversari, et al., Immunogenetics 35:145 (1992).
van der Bruggen et al., Science 254:1643–1647 (1991).
Ignacio et al., Brain Research 529:42–49 (1990).
Newgard et al., J. Biol. Chem., 263:3850–3857.
Rammensee et al., Immunogenetics 41:178–228 (1995).
Van den Eynde et al., Curr. Opinion in Immun. 7:674–681 (1995).
Gelinas et al., Mol. Brain Res. 6:177–185 (1989).
Boscoe et al., Mol. Brain Res. 10:273–275 (1991).
Rabitzsch et al., Immunoenzymometric Assay of Human Glycogen Phosphorylase Isoenzyme BB in Diagnosis of Ischemic Myocardial Injury, Clin. Chem. 966–978 (1995).
Crerar, J. Biol. Chem., 270:13748–13756 (1995).

*Primary Examiner*—Marianne P. Allen
*Attorney, Agent, or Firm*—Wolf, Greenfield & Sacks, P.C.

[57] ABSTRACT

The invention describes brain glycogen phosphorylase tumor rejection antigen precursors, including nucleic acids encoding such tumor rejection antigen precursors, tumor rejection antigen peptides or precursors thereof and antibodies relating thereto. Methods and products also are provided for diagnosing and treating conditions characterized by expression of a brain glycogen phosphorylase tumor rejection antigen or precursor thereof.

24 Claims, 6 Drawing Sheets

6,096,520

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 110 base pairs
      (B) TYPE: nucleic acid
      (C) STRANDEDNESS: double (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
         (A) ORGANISM: Homo sapiens (xi) SEQUENCE DESCRIPTION: SEQ ID NO:1:

ATGGGCGAAC CGCTGACGGA CAGCGAGAAG CGGAAGCAGA TCAGCGTGCG CGGCCTGGCG      60

GGGCTAGGCG ACGTGGCCGA GGTGCGGAAG AGCTTCAACC GGCACTTGCA                110

(2) INFORMATION FOR SEQ ID NO:2:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
         (A) ORGANISM: Homo sapiens (xi) SEQUENCE DESCRIPTION: SEQ ID NO:2:

ATGGGCGAAC CGCTGACGGA CAGCGAGAAG CGGAAGCAGA TCAGCGTGCG CGGCCTGGCG      60

GGGCTAGGCG ACGTGGCCGA GGTGCGGAAG AGCTTCAACC GG                        102

(2) INFORMATION FOR SEQ ID NO:3:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
         (A) ORGANISM: Homo sapiens (xi) SEQUENCE DESCRIPTION: SEQ ID NO:3:

ATGGGCGAAC CGCTGACGGA CAGCGAGAAG CGGAAGCAGA TCAGCGTGCG CGGCCTGGCG      60

GGGCTAGGCG ACGTGGCCGA G                                                81

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Homo sapiens (xi) SEQUENCE DESCRIPTION: SEQ ID NO:4:

Gly Leu Ala Gly Leu Gly Asp Val Ala Glu Val Arg Lys Ser Phe Asn
1               5                  10                  15

Arg (2) INFORMATION FOR SEQ ID NO:5:

(i) SEQUENCE CHARACTERISTICS:
             (A) LENGTH: 11 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Homo sapiens (xi) SEQUENCE DESCRIPTION: SEQ ID NO:5:

Gly Leu Ala Gly Leu Gly Asp Val Ala Glu Val
1               5                  10

(2) INFORMATION FOR SEQ ID NO:6:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: Homo sapiens (xi) SEQUENCE DESCRIPTION: SEQ ID NO:6:

Ala Gly Leu Gly Asp Val Ala Glu Val Arg
1               5                  10

(2) INFORMATION FOR SEQ ID NO:7:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide

```
        (iii) HYPOTHETICAL: NO (iv) ANTI-SENSE: NO (v) FRAGMENT TYPE: internal (vi) ORIGINAL SOURCE:
             (A) ORGANISM: Homo sapiens (xi) SEQUENCE DESCRIPTION: SEQ ID NO:7:

Gly Leu Gly Asp Val Ala Glu Val Arg Lys
1               5                   10

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Homo sapiens (xi) SEQUENCE DESCRIPTION: SEQ ID NO:8:

Leu Gly Asp Val Ala Glu Val Arg Lys Ser
1               5                   10

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Homo sapiens (xi) SEQUENCE DESCRIPTION: SEQ ID NO:9:

Gly Asp Val Ala Glu Val Arg Lys Ser Phe
1               5                   10

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO
```

```
        (v) FRAGMENT TYPE: internal (vi) ORIGINAL SOURCE:
            (A) ORGANISM: Homo sapiens (xi) SEQUENCE DESCRIPTION: SEQ ID NO:10:

Asp Val Ala Glu Val Arg Lys Ser Phe Asn
1               5                   10

(2) INFORMATION FOR SEQ ID NO:11:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Homo sapiens (xi) SEQUENCE DESCRIPTION: SEQ ID NO:11:

Val Ala Glu Val Arg Lys Ser Phe Asn Arg
1               5                   10

(2) INFORMATION FOR SEQ ID NO:12:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Homo sapiens (xi) SEQUENCE DESCRIPTION: SEQ ID NO:12:

Leu Ala Gly Leu Gly Asp Val Ala Glu Val
1               5                   10

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
```

```
          (A) ORGANISM: Homo sapiens (xi) SEQUENCE DESCRIPTION: SEQ ID NO:13:

Ala Gly Leu Gly Asp Val Ala Glu Val
1               5

(2) INFORMATION FOR SEQ ID NO:14:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: Homo sapiens (xi) SEQUENCE DESCRIPTION: SEQ ID NO:14:

Gly Leu Gly Asp Val Ala Glu Val
1               5

(2) INFORMATION FOR SEQ ID NO:15:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: Homo sapiens (xi) SEQUENCE DESCRIPTION: SEQ ID NO:15:

Leu Gly Asp Val Ala Glu Val
1               5

(2) INFORMATION FOR SEQ ID NO:16:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: Homo sapiens (xi) SEQUENCE DESCRIPTION: SEQ ID NO:16:
```

Gly Asp Val Ala Glu Val
1               5

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:17:

TGCCAGGCAC AGGTGGACCA                                            20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:18:

CAGACCCCAG AATCCAGAGG C                                          21

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Homo sapiens (xi) SEQUENCE DESCRIPTION: SEQ ID NO:19:

Gly Ile Val Gly Val Glu Asn Val Ala Glu Leu
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single -continued (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Homo sapiens (xi) SEQUENCE DESCRIPTION: SEQ ID NO:20:

Gly Leu Ala Gly Val Glu Asn Val Ile Glu Leu
1               5                   10

(2) INFORMATION FOR SEQ ID NO:21:

(i) SEQUENCE CHARACTERISTICS:
        (A) LENGTH: 4066 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 35..2566

(xi) SEQUENCE DESCRIPTION: SEQ ID NO:21:

```
CCTCCATCTC TTTTCCTCCG CCTCCGCCGG CGCG ATG GGC GAA CCG CTG ACG          52
                                     Met Gly Glu Pro Leu Thr
                                       1               5

GAC AGC GAG AAG CGG AAG CAG ATC AGC GTG CGC GGC CTG GCG GGG CTA       100
Asp Ser Glu Lys Arg Lys Gln Ile Ser Val Arg Gly Leu Ala Gly Leu
            10                  15                  20

GGC GAC GTG GCC GAG GTG CGG AAG AGC TTC AAC CGG CAC TTG CAC TTC       148
Gly Asp Val Ala Glu Val Arg Lys Ser Phe Asn Arg His Leu His Phe
        25                  30                  35

ACG CTG GTC AAG GAC CGC AAT GTG GCC ACG CCC CGC GAC TAC TTC TTC       196
Thr Leu Val Lys Asp Arg Asn Val Ala Thr Pro Arg Asp Tyr Phe Phe
    40                  45                  50

GCG CTG GCG CAC ACG GTG CGC GAC CAC CTC GTG GGC CGC TGG ATC CGC       244
Ala Leu Ala His Thr Val Arg Asp His Leu Val Gly Arg Trp Ile Arg
55                  60                  65                  70

ACG CAG CAG CAC TAC TAC GAG CGC GAC CCC AAG CGC ATT TAT TAT CTT       292
Thr Gln Gln His Tyr Tyr Glu Arg Asp Pro Lys Arg Ile Tyr Tyr Leu
                75                  80                  85

TCC CTG GAA TTC TAC ATG GGT CGC ACG CTG CAG AAC ACG ATG GTG AAC       340
Ser Leu Glu Phe Tyr Met Gly Arg Thr Leu Gln Asn Thr Met Val Asn
            90                  95                 100

CTG GGC CTT CAG AAT GCC TGC GAT GAA GCC ATC TAT CAG TTG GGG TTA       388
Leu Gly Leu Gln Asn Ala Cys Asp Glu Ala Ile Tyr Gln Leu Gly Leu
        105                 110                 115

GAC TTG GAG GAA CTC GAG GAG ATA GAA GAA GAT GCT GGC CTT GGG AAT       436
Asp Leu Glu Glu Leu Glu Glu Ile Glu Glu Asp Ala Gly Leu Gly Asn
    120                 125                 130

GGA GGC CTG GGG AGG CTG GCA GCG TGT TTC CTT GAC TCA ATG GCT ACC       484
```

```
Gly Gly Leu Gly Arg Leu Ala Ala Cys Phe Leu Asp Ser Met Ala Thr
135                 140                 145                 150

TTG GGC CTG GCA GCA TAC GGC TAT GGA ATC CGC TAT GAA TTT GGG ATT    532
Leu Gly Leu Ala Ala Tyr Gly Tyr Gly Ile Arg Tyr Glu Phe Gly Ile
                    155                 160                 165

TTT AAC CAG AAG ATT GTC AAT GGC TGG CAG GTA GAG GAG GCC GAT GAC    580
Phe Asn Gln Lys Ile Val Asn Gly Trp Gln Val Glu Glu Ala Asp Asp
                170                 175                 180

TGG CTG CGC TAC GGC AAC CCC TGG GAG AAA GCG CGG CCT GAG TAT ATG    628
Trp Leu Arg Tyr Gly Asn Pro Trp Glu Lys Ala Arg Pro Glu Tyr Met
            185                 190                 195

CTT CCC GTG CAC TTC TAC GGA CGC GTG GAG CAC ACC CCC GAC GGC GTG    676
Leu Pro Val His Phe Tyr Gly Arg Val Glu His Thr Pro Asp Gly Val
        200                 205                 210

AAG TGG CTG GAC ACA CAG GTG GTG CTG GCC ATG CCC TAC GAC ACC CCA    724
Lys Trp Leu Asp Thr Gln Val Val Leu Ala Met Pro Tyr Asp Thr Pro
215                 220                 225                 230

GTG CCC GGC TAC AAG AAC AAC ACC GTC AAC ACC ATG CGG CTG TGG TCC    772
Val Pro Gly Tyr Lys Asn Asn Thr Val Asn Thr Met Arg Leu Trp Ser
                235                 240                 245

GCC AAG GCT CCC AAC GAC TTC AAG CTG CAG GAC TTC AAC GTG GGA GAC    820
Ala Lys Ala Pro Asn Asp Phe Lys Leu Gln Asp Phe Asn Val Gly Asp
                250                 255                 260

TAC ATC GAG GCG GTC CTG GAC CGG AAC TTG GCT GAG AAC ATC TCC AGG    868
Tyr Ile Glu Ala Val Leu Asp Arg Asn Leu Ala Glu Asn Ile Ser Arg
            265                 270                 275

GTC CTG TAT CCA AAT GAT AAC TTC TTT GAG GGG AAG GAG CTG CGG CTG    916
Val Leu Tyr Pro Asn Asp Asn Phe Phe Glu Gly Lys Glu Leu Arg Leu
        280                 285                 290

AAG CAG GAG TAC TTC GTG GTG GCC GCC ACG CTC CAG GAC ATC ATC CGC    964
Lys Gln Glu Tyr Phe Val Val Ala Ala Thr Leu Gln Asp Ile Ile Arg
295                 300                 305                 310

CGC TTC AAG TCG TCC AAG TTC GGC TGC CGG GAC CCT GTG AGA ACC TGT   1012
Arg Phe Lys Ser Ser Lys Phe Gly Cys Arg Asp Pro Val Arg Thr Cys
                315                 320                 325

TTC GAG ACG TTC CCA GAC AAG GTG GCC ATC CAG CTG AAC GAC ACC CAC   1060
Phe Glu Thr Phe Pro Asp Lys Val Ala Ile Gln Leu Asn Asp Thr His
                330                 335                 340

CCC GCC CTC TCC ATC CCT GAG CTC ATG CGG ATC CTG GTG GAC GTG GAG   1108
Pro Ala Leu Ser Ile Pro Glu Leu Met Arg Ile Leu Val Asp Val Glu
            345                 350                 355

AAG GTG GAC TGG GAC AAG GCC TGG GAA ATC ACG AAG AAG ACC TGT GCA   1156
Lys Val Asp Trp Asp Lys Ala Trp Glu Ile Thr Lys Lys Thr Cys Ala
        360                 365                 370

TAC ACC AAC CAC ACT GTG CTG CCT GAG GCC TTG GAG CGC TGG CCC GTG   1204
Tyr Thr Asn His Thr Val Leu Pro Glu Ala Leu Glu Arg Trp Pro Val
375                 380                 385                 390

TCC ATG TTT GAG AAG CTG CTG CCG CGG CAC CTG GAG ATA ATC TAT GCC   1252
Ser Met Phe Glu Lys Leu Leu Pro Arg His Leu Glu Ile Ile Tyr Ala
                395                 400                 405

ATC AAC CAG CGG CAC CTG GAC CAC GTG GCC GCG CTG TTT CCC GGC GAT   1300
Ile Asn Gln Arg His Leu Asp His Val Ala Ala Leu Phe Pro Gly Asp
                410                 415                 420

GTG GAC CGC CTG CGC AGG ATG TCT GTG ATC GAG GAG GGG GAC TGC AAG   1348
Val Asp Arg Leu Arg Arg Met Ser Val Ile Glu Glu Gly Asp Cys Lys
            425                 430                 435

CGG ATC AAC ATG GCC CAC CTG TGT GTG ATT GGG TCC CAT GCT GTC AAT   1396
Arg Ile Asn Met Ala His Leu Cys Val Ile Gly Ser His Ala Val Asn
        440                 445                 450
```

```
                                                    -continued

GGT GTG GCG AGG ATC CAC TCG GAG ATC GTG AAA CAG TCG GTC TTT AAG    1444
Gly Val Ala Arg Ile His Ser Glu Ile Val Lys Gln Ser Val Phe Lys
455                 460                 465                 470

GAT TTT TAT GAA CTG GAG CCA GAG AAG TTC CAG AAT AAG ACC AAT GGC    1492
Asp Phe Tyr Glu Leu Glu Pro Glu Lys Phe Gln Asn Lys Thr Asn Gly
                475                 480                 485

ATC ACC CCC CGC CGG TGG CTG CTG CTG TGC AAC CCG GGG CTG GCC GAT    1540
Ile Thr Pro Arg Arg Trp Leu Leu Leu Cys Asn Pro Gly Leu Ala Asp
            490                 495                 500

ACC ATC GTG GAG AAA ATT GGG GAG GAG TTC CTG ACT GAC CTG AGC CAG    1588
Thr Ile Val Glu Lys Ile Gly Glu Glu Phe Leu Thr Asp Leu Ser Gln
        505                 510                 515

CTG AAG AAG CTG CTG CCG CTG GTC AGT GAC GAG GTG TTC ATC AGG GAC    1636
Leu Lys Lys Leu Leu Pro Leu Val Ser Asp Glu Val Phe Ile Arg Asp
    520                 525                 530

GTG GCC AAG GTC AAA CAG GAG AAC AAG CTC AAG TTC TCG GCC TTC CTG    1684
Val Ala Lys Val Lys Gln Glu Asn Lys Leu Lys Phe Ser Ala Phe Leu
535                 540                 545                 550

GAG AAG GAG TAC AAG GTG AAG ATC AAC CCC TCC TCC ATG TTC GAT GTG    1732
Glu Lys Glu Tyr Lys Val Lys Ile Asn Pro Ser Ser Met Phe Asp Val
                555                 560                 565

CAT GTG AAG AGG ATC CAC GAG TAC AAG CGG CAG CTG CTC AAC TGC CTG    1780
His Val Lys Arg Ile His Glu Tyr Lys Arg Gln Leu Leu Asn Cys Leu
            570                 575                 580

CAC GTC GTC ACC CTG TAC AAT CGA ATC AAG AGA GAC CCG GCC AAG GCT    1828
His Val Val Thr Leu Tyr Asn Arg Ile Lys Arg Asp Pro Ala Lys Ala
        585                 590                 595

TTT GTG CCC AGG ACT GTT ATG ATT GGG GGC AAG GCA GCG CCC GGT TAC    1876
Phe Val Pro Arg Thr Val Met Ile Gly Gly Lys Ala Ala Pro Gly Tyr
    600                 605                 610

CAC ATG GCC AAG CTG ATC ATC AAG TTG GTC ACC TCC ATC GGC GAC GTC    1924
His Met Ala Lys Leu Ile Ile Lys Leu Val Thr Ser Ile Gly Asp Val
615                 620                 625                 630

GTC AAT CAT GAC CCA GTT GTG GGT GAC AGG TTG AAA GTG ATC TTC CTG    1972
Val Asn His Asp Pro Val Val Gly Asp Arg Leu Lys Val Ile Phe Leu
                635                 640                 645

GAG AAC TAC CGT GTG TCC TTG GCT GAG AAA GTG ATC CCG GCC GCT GAT    2020
Glu Asn Tyr Arg Val Ser Leu Ala Glu Lys Val Ile Pro Ala Ala Asp
            650                 655                 660

CTG TCG CAG CAG ATC TCC ACT GCA GGC ACC GAG GCC TCA GGC ACA GGC    2068
Leu Ser Gln Gln Ile Ser Thr Ala Gly Thr Glu Ala Ser Gly Thr Gly
        665                 670                 675

AAC ATG AAG TTC ATG CTC AAC GGG GCC CTC ACC ATC GGC ACC ATG GAC    2116
Asn Met Lys Phe Met Leu Asn Gly Ala Leu Thr Ile Gly Thr Met Asp
    680                 685                 690

GGC GCC AAC GTG GAG ATG GCC GAG GAG GCC GGG GCC GAG AAC CTC TTC    2164
Gly Ala Asn Val Glu Met Ala Glu Glu Ala Gly Ala Glu Asn Leu Phe
695                 700                 705                 710

ATC TTC GGC CTG CGG GTG GAG GAT GTC GAG GCC TTG GAC CGG AAA GGG    2212
Ile Phe Gly Leu Arg Val Glu Asp Val Glu Ala Leu Asp Arg Lys Gly
                715                 720                 725

TAC AAT GCC AGG GAG TAC TAC GAC CAC CTG CCC GAG CTG AAG CAG GCC    2260
Tyr Asn Ala Arg Glu Tyr Tyr Asp His Leu Pro Glu Leu Lys Gln Ala
            730                 735                 740

GTG GAC CAG ATC AGC AGT GGC TTT TTT TCT CCC AAG GAG CCA GAC TGC    2308
Val Asp Gln Ile Ser Ser Gly Phe Phe Ser Pro Lys Glu Pro Asp Cys
        745                 750                 755

TTC AAG GAC ATC GTG AAC ATG CTG ATG CAC CAT GAC AGG TTC AAG GTG    2356
Phe Lys Asp Ile Val Asn Met Leu Met His His Asp Arg Phe Lys Val
    760                 765                 770
```

```
TTT GCA GAC TAT GAA GCC TAC ATG CAG TGC CAG GCA CAG GTG GAC CAG    2404
Phe Ala Asp Tyr Glu Ala Tyr Met Gln Cys Gln Ala Gln Val Asp Gln
775                 780                 785                 790

CTG TAC CGG AAC CCC AAG GAG TGG ACC AAG AAG GTC ATC AGG AAC ATC    2452
Leu Tyr Arg Asn Pro Lys Glu Trp Thr Lys Lys Val Ile Arg Asn Ile
                795                 800                 805

GCC TGC TCG GGC AAG TTC TCC AGT GAC CGG ACC ATC ACG GAG TAT GCA    2500
Ala Cys Ser Gly Lys Phe Ser Ser Asp Arg Thr Ile Thr Glu Tyr Ala
            810                 815                 820

CGG GAG ATC TGG GGT GTG GAG CCC TCC GAC CTG CAG ATC CCG CCC CCC    2548
Arg Glu Ile Trp Gly Val Glu Pro Ser Asp Leu Gln Ile Pro Pro Pro
        825                 830                 835

AAC ATC CCC CGG GAC TAGGCACACC CTGCCTTGGC GGGACCAGCG GGCATTTGTT    2603
Asn Ile Pro Arg Asp
    840

TTCTTGCTGA CTTTGCACCT CCTTTTTTCC CCAAACACTT TGCCAGCCAC TGGTGGTCCC    2663

TGCTTTTCTG AGTACCATGT TTCCAGGAGG GGCCATGGGG GTCAGGGTGG TTTTGAGAGA    2723

GCAGGGTAAG GAAGGAATGT GCTAGAAGTG CTCCTAGTTT CTTGTAAAGG AAGCCAGAGT    2783

TGACAGTACA AAGGGTCGTG GCCAGCCCTG CAGCTTCAGC ACCTGCCCCA CCCAGAGTGG    2843

GAGTCAGGTG GAGCCACCTG CTGGGCTCCC CCAGAACTTT GCACACATCT TGCTATGTAT    2903

TAGCCGATGT CTTTAGTGTT GAGCCTCTGG ATTCTGGGGT CTGGGCCAGT GGCCATAGTG    2963

AAGCCTGGGA ATGAGTGTTA CTGCAGCATC TGGGCTGCCA GCCACAGGGA AGGGCCAAGC    3023

CCCATGTAGC CCCAGTCATC CTGCCCAGCC CTGCCTCCTG GCCATGCCGG GAGGGGTCGG    3083

ATCCTCTAGG CATCGCCTTC ACAGCCCCCT GCCCCCTGCC CTCTGTCCTG GCTCTGCACC    3143

TGGTATATGG GTCATGGACC AGATGGGGCT TTCCCTTTGT AGCCATCCAA TGGGCATTGT    3203

GTGGGTGCTT GGAACCCGGG ATGACTGAGG GGGACACTGG AGTGGGTGCT TGTGTCTGCT    3263

GTCTCAGAGG CCTTGGTCAG GATGAAGTTG GCTGACACAG CTTAGCTTGG TTTTGCTTAT    3323

TCAAAAGAGA AAATAACTAC ACATGGAAAT GAAACTAGCT GAAGCTTTTT CTTGTTTTAG    3383

CAACTGAAAA TTGTACTTGG TCACTTTTGT GCTTGAGGAG GCCCATTTTC TGCCTGGCAG    3443

GGGCAGGTCT GTGCCCTCCC GCTTGACTCC TGCTGTGTCC TGAGGTGCAT TTCCTGTTTG    3503

TTACACACAA GGGCCAGGCT CCATTCTCCC TCCCTTTCCA CCAGTGCCAC AGCCTCGTCT    3563

GGAAAAAGGA CCAGGGGTCC CGGAGGAACC CATTTGTGCT CTGCTTGGAC AGCAGGCCTG    3623

GCACTGGGAG GTGGGGGTGA GCCCCTCACA GCCTTGCCCC TCCCCAAGGC TCGAACCTGC    3683

CTCCCATTGC CAAGAGAGA GGGCAGGGAA CAGGCTACTG TCCTTCCCTG TGGAATTGCC    3743

GAGAAATCTA GCACCTTGCA TGCTGGATCT GGGCTGCGGG GAGGCTCTTT TTCTCCCTGG    3803

CCTCCAGTGC CCACCAGGAG GATCTGCGCA CGGTGCACAG CCCACCGAG CACTACAGCC    3863

TTTTATTGAG TGGGGCAAGT GCTGGGCTGT GGTCGTGCCC TGACAGCATC TTCCCCAGGC    3923

AGCGGCTCTG TGGAGGAGGC CATACTCCCC TAGTTGGCCA CTGGGCCAC CACCCTGACC    3983

ACCACTGTGC CCCTCATTGT TACTGCCTTG TGAGATAAAA ACTGATTAAA CCTTTGTGGC    4043

TGTGGTTGGC TGAAAAAAAA AAA                                           4066

(2) INFORMATION FOR SEQ ID NO:22:

(i) SEQUENCE CHARACTERISTICS:
         (A) LENGTH: 843 amino acids
         (B) TYPE: amino acid
         (D) TOPOLOGY: linear
```

(ii) MOLECULE TYPE: protein (xi) SEQUENCE DESCRIPTION: SEQ ID NO:22:

| | | | | | | | | | | | | | | | |
|---|---|---|---|---|---|---|---|---|---|---|---|---|---|---|---|
|Met|Gly|Glu|Pro|Leu|Thr|Asp|Ser|Glu|Lys|Arg|Lys|Gln|Ile|Ser|Val|
|1| | | |5| | | | |10| | | | |15| |

Arg Gly Leu Ala Gly Leu Gly Asp Val Ala Glu Val Arg Lys Ser Phe
            20                  25                  30

Asn Arg His Leu His Phe Thr Leu Val Lys Asp Arg Asn Val Ala Thr
            35                  40                  45

Pro Arg Asp Tyr Phe Phe Ala Leu Ala His Thr Val Arg Asp His Leu
        50                  55                  60

Val Gly Arg Trp Ile Arg Thr Gln Gln His Tyr Tyr Glu Arg Asp Pro
65                  70                  75                  80

Lys Arg Ile Tyr Tyr Leu Ser Leu Glu Phe Tyr Met Gly Arg Thr Leu
                85                  90                  95

Gln Asn Thr Met Val Asn Leu Gly Leu Gln Asn Ala Cys Asp Glu Ala
            100                 105                 110

Ile Tyr Gln Leu Gly Leu Asp Leu Glu Glu Leu Glu Glu Ile Glu Glu
            115                 120                 125

Asp Ala Gly Leu Gly Asn Gly Gly Leu Gly Arg Leu Ala Ala Cys Phe
        130                 135                 140

Leu Asp Ser Met Ala Thr Leu Gly Leu Ala Ala Tyr Gly Tyr Gly Ile
145                 150                 155                 160

Arg Tyr Glu Phe Gly Ile Phe Asn Gln Lys Ile Val Asn Gly Trp Gln
                165                 170                 175

Val Glu Glu Ala Asp Asp Trp Leu Arg Tyr Gly Asn Pro Trp Glu Lys
            180                 185                 190

Ala Arg Pro Glu Tyr Met Leu Pro Val His Phe Tyr Gly Arg Val Glu
            195                 200                 205

His Thr Pro Asp Gly Val Lys Trp Leu Asp Thr Gln Val Val Leu Ala
        210                 215                 220

Met Pro Tyr Asp Thr Pro Val Pro Gly Tyr Lys Asn Asn Thr Val Asn
225                 230                 235                 240

Thr Met Arg Leu Trp Ser Ala Lys Ala Pro Asn Asp Phe Lys Leu Gln
                245                 250                 255

Asp Phe Asn Val Gly Asp Tyr Ile Glu Ala Val Leu Asp Arg Asn Leu
            260                 265                 270

Ala Glu Asn Ile Ser Arg Val Leu Tyr Pro Asn Asp Asn Phe Phe Glu
            275                 280                 285

Gly Lys Glu Leu Arg Leu Lys Gln Glu Tyr Phe Val Val Ala Ala Thr
        290                 295                 300

Leu Gln Asp Ile Ile Arg Arg Phe Lys Ser Ser Lys Phe Gly Cys Arg
305                 310                 315                 320

Asp Pro Val Arg Thr Cys Phe Glu Thr Phe Pro Asp Lys Val Ala Ile
                325                 330                 335

Gln Leu Asn Asp Thr His Pro Ala Leu Ser Ile Pro Glu Leu Met Arg
            340                 345                 350

Ile Leu Val Asp Val Glu Lys Val Asp Trp Asp Lys Ala Trp Glu Ile
            355                 360                 365

Thr Lys Lys Thr Cys Ala Tyr Thr Asn His Thr Val Leu Pro Glu Ala
        370                 375                 380

Leu Glu Arg Trp Pro Val Ser Met Phe Glu Lys Leu Leu Pro Arg His
385                 390                 395                 400

-continued

```
Leu Glu Ile Ile Tyr Ala Ile Asn Gln Arg His Leu Asp His Val Ala
            405                 410                 415
Ala Leu Phe Pro Gly Asp Val Asp Arg Leu Arg Arg Met Ser Val Ile
            420                 425                 430
Glu Glu Gly Asp Cys Lys Arg Ile Asn Met Ala His Leu Cys Val Ile
            435                 440                 445
Gly Ser His Ala Val Asn Gly Val Ala Arg Ile His Ser Glu Ile Val
450                     455                 460
Lys Gln Ser Val Phe Lys Asp Phe Tyr Glu Leu Glu Pro Glu Lys Phe
465                 470                  475                 480
Gln Asn Lys Thr Asn Gly Ile Thr Pro Arg Arg Trp Leu Leu Leu Cys
                485                 490                 495
Asn Pro Gly Leu Ala Asp Thr Ile Val Glu Lys Ile Gly Glu Glu Phe
            500                 505                 510
Leu Thr Asp Leu Ser Gln Leu Lys Lys Leu Leu Pro Leu Val Ser Asp
            515                 520                 525
Glu Val Phe Ile Arg Asp Val Ala Lys Val Lys Gln Glu Asn Lys Leu
            530                 535                 540
Lys Phe Ser Ala Phe Leu Glu Lys Glu Tyr Lys Val Lys Ile Asn Pro
545                 550                 555                 560
Ser Ser Met Phe Asp Val His Val Lys Arg Ile His Glu Tyr Lys Arg
                565                 570                 575
Gln Leu Leu Asn Cys Leu His Val Thr Leu Tyr Asn Arg Ile Lys
                580                 585                 590
Arg Asp Pro Ala Lys Ala Phe Val Pro Arg Thr Val Met Ile Gly Gly
            595                 600                 605
Lys Ala Ala Pro Gly Tyr His Met Ala Lys Leu Ile Ile Lys Leu Val
            610                 615                 620
Thr Ser Ile Gly Asp Val Val Asn His Asp Pro Val Val Gly Asp Arg
625                 630                 635                 640
Leu Lys Val Ile Phe Leu Glu Asn Tyr Arg Val Ser Leu Ala Glu Lys
                645                 650                 655
Val Ile Pro Ala Ala Asp Leu Ser Gln Gln Ile Ser Thr Ala Gly Thr
            660                 665                 670
Glu Ala Ser Gly Thr Gly Asn Met Lys Phe Met Leu Asn Gly Ala Leu
            675                 680                 685
Thr Ile Gly Thr Met Asp Gly Ala Asn Val Glu Met Ala Glu Glu Ala
            690                 695                 700
Gly Ala Glu Asn Leu Phe Ile Phe Gly Leu Arg Val Glu Asp Val Glu
705                 710                 715                 720
Ala Leu Asp Arg Lys Gly Tyr Asn Ala Arg Glu Tyr Tyr Asp His Leu
                725                 730                 735
Pro Glu Leu Lys Gln Ala Val Asp Gln Ile Ser Ser Gly Phe Phe Ser
            740                 745                 750
Pro Lys Glu Pro Asp Cys Phe Lys Asp Ile Val Asn Met Leu Met His
            755                 760                 765
His Asp Arg Phe Lys Val Phe Ala Asp Tyr Glu Ala Tyr Met Gln Cys
            770                 775                 780
Gln Ala Gln Val Asp Gln Leu Tyr Arg Asn Pro Lys Glu Trp Thr Lys
785                 790                 795                 800
Lys Val Ile Arg Asn Ile Ala Cys Ser Gly Lys Phe Ser Ser Asp Arg
                805                 810                 815
Thr Ile Thr Glu Tyr Ala Arg Glu Ile Trp Gly Val Glu Pro Ser Asp
```

```
              820                 825                 830
Leu Gln Ile Pro Pro Pro Asn Ile Pro Arg Asp
         835                 840

(2) INFORMATION FOR SEQ ID NO:23:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
         (A) ORGANISM: Homo sapiens (xi) SEQUENCE DESCRIPTION: SEQ ID NO:23:

GGGCTAGGCG ACGTGGCCGA GGTG                                                   24

(2) INFORMATION FOR SEQ ID NO:24:

(i) SEQUENCE CHARACTERISTICS:
         (A) LENGTH: 27 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
         (A) ORGANISM: Homo sapiens (xi) SEQUENCE DESCRIPTION: SEQ ID NO:24:

GCGGGGCTAG GCGACGTGGC CGAGGTG                                                27

(2) INFORMATION FOR SEQ ID NO:25:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
         (A) ORGANISM: Homo sapiens (xi) SEQUENCE DESCRIPTION: SEQ ID NO:25:

CTGGCGGGGC TAGGCGACGT GGCCGAGGTG                                             30
```

BRAIN GLYCOGEN PHOSPHORYLASE CANCER ANTIGEN

RELATED APPLICATIONS

This application is a continuation of Ser. No. 08/672,351, filed Jun. 25, 1996, now abandoned entitled Brain Glycogen Phosphorylase Cancer Antigen.

FIELD OF THE INVENTION

This invention relates to tumor rejection antigens and precursors thereof. The tumor rejection antigen precursors are processed, inter alia, into at least one tumor rejection antigen that is presented by HLA molecules. The invention also relates to nucleic acid molecules which code for tumor rejection antigens and precursors thereof. The nucleic acid molecules, proteins coded for by such molecules and peptides derived therefrom, as well as related antibodies and cytotoxic lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response. T cells can recognize and interact with other cells via cell surface complexes on the other cells of peptides and molecules referred to as human leukocyte antigens ("HLA") or major histocompatibility complexes ("MHCs"). The peptides are derived from larger molecules which are processed by the cells which also present the HLA/MHC molecule. See Male et al., *Advanced Immunology* (J.P. Lipincott Company, 1987), especially chapters 6–10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities.

The mechanism by which T cells recognize alien materials also has been implicated in cancer. A number of cytolytic T lymphocyte (CTL) clones directed against autologous melanoma have been described. In some instances, the antigens recognized by these clones have been characterized. In PCT application PCT/US92/04354, published on Nov. 26, 1992, the "MAGE" family, a tumor specific family of genes, is disclosed. The expression products of these genes are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. Pat. No. 5,342,774.

In U.S. Pat. No. 5,405,940, MAGE nonapeptides are taught which are presented by the HLA-A1 molecule. Given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

It also was discovered that a MAGE expression product is processed to a second TRA. This second TRA is presented by HLA-C clone 10 molecules. Therefore, a given TRAP can yield a plurality of TRAs.

In PCT WO94/14459, published Jul. 7, 1994, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In PCT WO94/21126, published Sep. 29, 1994, a second TRA, not derived from tyrosinase is taught to be presented by HLA-A2 molecules. The TRA is derived from a TRAP, but is coded for by a non-MAGE gene. It is called Melan-A. This disclosure shows that a particular HLA molecule may present TRAs derived from different sources.

In PCT WO95/00159, published Jan. 5, 1995, an unrelated tumor rejection antigen precursor, the so-called "BAGE" precursor, is described. TRAs are derived from the TRAP and also are described. They form complexes with MHC molecule HLA-C-Clone 10.

In PCT WO95/03422, published Feb. 2, 1995, another unrelated tumor rejection antigen precursor, the so-called "GAGE" precursor, is described. The GAGE precursor is not related to the BAGE or the MAGE family.

The work which is presented by the papers, patents and patent applications described above deal, for the most part, with the MAGE family of genes, the BAGE gene and the GAGE gene. These genes are expressed in a number of tumors but are completely silent in normal tissues except testis. None is expressed in renal carcinoma.

Recently another unrelated tumor rejection antigen precursor, the "RAGE" precursor, was discovered. It is distinguished, inter alia, by its expression in certain renal carcinomas. The RAGE precursor is not related to the GAGE, BAGE or MAGE family.

The brain glycogen phosphorylase gene is normally expressed in the adult in brain and retinal pigment epithelium. It previously was reported that this gene was overexpressed in certain renal, hepatoma and stomach cancers. It was not reported, however, that the brain glycogen phosphorylase gene was capable of provoking autologous CTL proliferation with specificity for brain glycogen phosphorylase peptides complexed with HLA. In other words, brain glycogen phosphorylase was not known as a TRAP.

It has now been discovered that the brain glycogen phosphorylase gene is expressed in melanoma tumor cells, and in certain other tumor cell types. It now has been discovered that, the brain glycogen phosphorylase gene, encodes tumor rejection antigens and precursors thereof. The brain glycogen phosphorylase gene does not show homology to the MAGE family of genes, to the BAGE gene, the GAGE gene or to the RAGE gene.

The invention is elaborated upon in the disclosure which follows.

SUMMARY OF THE INVENTION

The invention provides isolated fragments of brain glycogen phosphorylase. The invention also provides isolated nucleic acid molecules, expression vectors containing those molecules and host cells transfected with those molecules. The foregoing, as well as brain glycogen phosphorylase itself, can be used in the diagnosis or treatment of conditions characterized by the expression of a brain glycogen phosphorylase TRA or TRAP.

According to one aspect of the invention, an isolated fragment of brain glycogen phosphorylase is provided. It includes at least the amino acid sequence of SEQ ID NO:15 and not more than 75% of the fill length brain glycogen phosphorylase, SEQ ID NO:22. In some embodiments, the isolated fragment includes not more than 100 amino acids. In other embodiments the isolated fragment may consist essentially of a molecule between 7 and 100 amino acids, which molecule comprises the sequence of SEQ ID NO:15. The isolated fragment may also consist essentially of a molecule having the sequence of SEQ ID NO: 15, SEQ ID NO:14, SEQ ID NO:13, SEQ ID NO:12, or SEQ ID NO:5. In some embodiments, the isolated fragment consists of a molecule having the sequence of SEQ ID NO:14, SEQ ID NO:13, or SEQ ID NO:12.

According to another aspect of the invention, an isolated nucleic acid molecule is provided. The molecule encodes a polypeptide selected from the group consisting of the fragments of brain glycogen phosphorylase disclosed above. Preferably the nucleic acids encode a polypeptide which consists essentially of a molecule having the sequence of SEQ ID NO:15, SEQ ID NO:14, SEQ ID NO:13, SEQ ID NO:12, or SEQ ID NO:5. In some embodiments, the polypeptide has a sequence selected from the group consisting of SEQ ID NO:14, SEQ ID NO:13 or SEQ ID NO:12.

According to another aspect of the invention, expression vectors and host cells containing those expression vectors are provided. The expression vectors include any one or more of the isolated nucleic acid molecules described above. In one embodiment, the expression vector comprises the isolated nucleic acid of SEQ ID NO:14, SEQ ID NO:13 or SEQ ID NO:12. Other expression vectors according to the invention include the isolated nucleic acids described above and a nucleic acid which codes for an HLA molecule which can present the brain glycogen phosphorylase tumor rejection antigens of the invention to cytolytic T cells. One example is HLA-A2. The host cells may endogenously express the HLA molecule such as HLA-A2.

According to another aspect of the invention, a method for enriching selectively a population of T cells with cytolytic T cells specific for a brain glycogen phosphorylase tumor rejection antigen is provided. The method involves contacting an isolated population of T cells with an agent presenting a complex of a brain glycogen phosphorylase tumor rejection antigen and an HLA presenting molecule. The T cells are contacted with the agent in an amount sufficient to selectively enrich the isolated population of T cells with the cytolytic T cells. In some embodiments, the HLA presenting molecule is HLA-A2 and the brain glycogen phosphorylase tumor rejection antigen is a peptide comprising the amino acids of SEQ ID NO:15. In other embodiments, the peptide is between 7 and 100 consecutive amino acids of SEQ ID NO:22. In preferred embodiments, the peptide consists essentially of a molecule having a sequence selected from the group consisting of SEQ ID NO:15, SEQ ID NO:14, SEQ ID NO:13, SEQ ID NO:12 and SEQ ID NO:5. Most preferably, the peptide has the sequence consisting of SEQ ID NO: 14, SEQ ID NO: 13, or SEQ ID NO: 12.

The recognition that brain glycogen phosphorylase peptides are presented by HLA molecules and recognized by CTLs permits diagnosis of certain disorders. Thus, according to still another aspect of the invention, a method for diagnosis of a disorder characterized by expression of a brain glycogen phosphorylase tumor rejection antigen is provided. The method involves contacting a biological sample isolated from a subject with an agent that is specific for the brain glycogen phosphorylase tumor rejection antigen. The biological sample is isolated from non-brain, and non-retinal pigment epithelium, tissue. The method then provides by determining the interaction between the agent and the brain glycogen phosphorylase tumor rejection antigen as a determination of the disorder. In one embodiment, the brain glycogen phosphorylase tumor rejection antigen is a peptide comprising the amino acids of SEQ ID NO:15. In other embodiments, the peptide is between 7 and 100 consecutive amino acids of SEQ. ID NO:22 and includes the amino acids of SEQ ID NO:15. Preferably, the peptide consists essentially of a molecule having a sequence selected from the group consisting of SEQ ID NO:15, SEQ ID NO:14, SEQ ID NO:13, SEQ ID NO:12 and SEQ ID NO:5. Most preferably, the sequence of the peptide consists of SEQ ID NO:14, SEQ ID NO:13, or SEQ ID NO:12.

The above-described method provides diagnosis of a disorder based on the presence of brain glycogen phosphorylase TRAs. Another aspect of the invention provides methods for diagnosing a disorder characterized by the expression of a brain glycogen phosphorylase tumor rejection antigen which forms a complex with HLA molecules. In some embodiments the complex is formed with HLA-A2. The method involves contacting a biological sample isolated from a subject with an agent that binds the complex and then determining binding between the complex and the agent as a determination of the disorder. In one embodiment, the brain glycogen phosphorylase tumor rejection antigen is a peptide comprising the amino acids of SEQ ID NO: 15. Preferably, the peptide consists essentially of a molecule having a sequence selected from the group consisting of SEQ ID NO: 15, SEQ ID NO: 14, SEQ ID NO: 13, SEQ ID NO: 12 and SEQ ID NO:5. In other preferred embodiments, the peptide consists of a molecule having a sequence selected from the group consisting of SEQ ID NO: 14, SEQ ID NO: 13, and SEQ ID NO: 12.

According to yet another aspect of the invention, methods for diagnosing a disorder characterized by expression of brain glycogen phosphorylase or nucleic acids which encode brain glycogen phosphorylase are provided. The methods involve isolating a biological sample from non-brain, non-retinal pigment epithelium, non-renal cell carcinoma, non-hepatoma and non-stomach adenocarcinoma tissue of a subject. In some embodiments, the methods involve contacting the biological sample with an agent that binds the brain glycogen phosphorylase and determining the binding between the brain glycogen phosphorylase and the agent as a determinant of the disorder. In other embodiments, the methods involve contacting the biological sample with an agent that is specific for the nucleic acid which encodes brain glycogen phosphorylase or an expression product thereof. The interaction between the agent and the nucleic acid or the expression product thereof is measured as a determination of the disorder.

In addition to diagnosis of disorders, treatment of certain disorders is also desirable. According to another aspect of the invention, a method for treating a subject with a disorder characterized by expression of a brain glycogen phosphorylase tumor rejection antigen is provided. The method involves administering to the subject an amount of an agent which enriches selectively in the subject the presence of complexes of HLA and brain glycogen phosphorylase tumor rejection antigen sufficient to ameliorate the disorder. Preferably the complexes are formed of HLA-A2 and a brain glycogen phosphorylase tumor rejection antigen. Preferably, the peptide consists essentially of a molecule having a sequence selected from the group consisting of SEQ ID NO:15, SEQ ID NO:14, SEQ ID NO:13, SEQ ID NO:12 and SEQ ID NO:5. In other preferred embodiments, the peptide consists of a molecule having a sequence selected from the group consisting of SEQ ID NO:14, SEQ ID NO:13, and SEQ ID NO:12. Another method involves administering to a subject in need of such treatment an amount of autologous cytolytic T cells sufficient to ameliorate the disorder, wherein the autologous cytolytic T cells are specific for complexes of an HLA molecule and a brain glycogen phosphorylase tumor rejection antigen. Preferably the complexes are formed of HLA-A2 and certain brain glycogen phosphorylase peptides as described above.

The invention in another aspect also provides pharmaceutical preparations containing the agents and/or cells of the preceding paragraph. In one embodiment, the preparation contains a pharmaceutically effective amount of brain glycogen phosphorylase or a fragment thereof that binds an HLA molecule along with pharmaceutically acceptable diluents, carriers or excipients. In some embodiments the HLA molecule is HLA-A2. Preferably, the brain glycogen phosphorylase or fragment thereof comprises a peptide having the amino acid sequence of SEQ ID NO:15. In another embodiment, the preparation contains a pharmaceutically effective amount of isolated autologous cytolytic T cells specific for complexes of an HLA molecule and a brain glycogen phosphorylase tumor rejection antigen.

According to another aspect of the invention, the use of isolated brain glycogen phosphorylase or fragments thereof in the manufacture of a medicament is provided. The fragments comprise the sequence of SEQ ID NO: 15. Preferred fragments of the brain glycogen phosphorylase molecules are described above. In certain embodiments, the medicament is an oral medicament, an inhalable medicament, or an injectable medicament.

According to another aspect of the invention, the use of brain glycogen phosphorylase or fragments thereof in the manufacture of a medicament for the treatment of cancer is provided.

According to another aspect of the invention, kits are provided. Such kits include at least separate portions of at least two of the previously discussed materials. Other components may be added, as desired. In some embodiments, kits comprising a separate portion of an isolated nucleic acid molecule which codes for a brain glycogen phosphorylase TRAP or a molecule including a brain glycogen phosphorylase TRA, and an HLA presenting molecule that forms a complex with that TRA and that stimulates a cytolytic T cell response. One such kit includes a nucleic acid which codes for the peptide of SEQ ID NO: 12, SEQ ID NO: 13 or SEQ ID NO: 14 and a nucleic acid molecule which codes for HLA-A2. Another kit according to the invention is an expression kit comprising a separate portion of the isolated nucleic acid molecule which codes for a brain glycogen phosphorylase TRAP or TRA, or an expression vector including a brain glycogen phosphorylase TRAP or TRA encoding nucleic acid and a nucleic acid molecule which codes for HLA-A2. In certain embodiments the kits include host cells which express an HLA molecule which presents a brain glycogen phosphorylase TRAP or TRA.

In connection with any of the isolated nucleic acids encoding a brain glycogen phosphorylase tumor rejection antigen as described above, the invention also embraces degenerate nucleic acids that differ from the isolated nucleic acid in codon sequence only due to the degeneracy of the genetic code or complements of any of the foregoing nucleic acids.

The invention also embraces functional variants and equivalents of all of the molecules described above.

These and other objects of the invention will be described in further detail in connection with the detailed description of the invention.

BRIEF DESCRIPTION OF THE DRAWINGS

FIG. 2 CTL lysis of T2 cells pulsed with peptides derived from brain glycogen phosphorylase.

FIG. 5A depict the results of a dose response assay in which melanoma cells from patient LB373, but not EBV-transformed B cells or peripheral blood lymphocytes from the same patient, are lysed by CTLs. FIG. 5B depicts a similar dose reponse assay in which T2 cells pulsed with a brain glycogen phosphorylase peptide are lysed by CTLs.

BRIEF DESCRIPTION OF THE SEQUENCES

Figure 1:
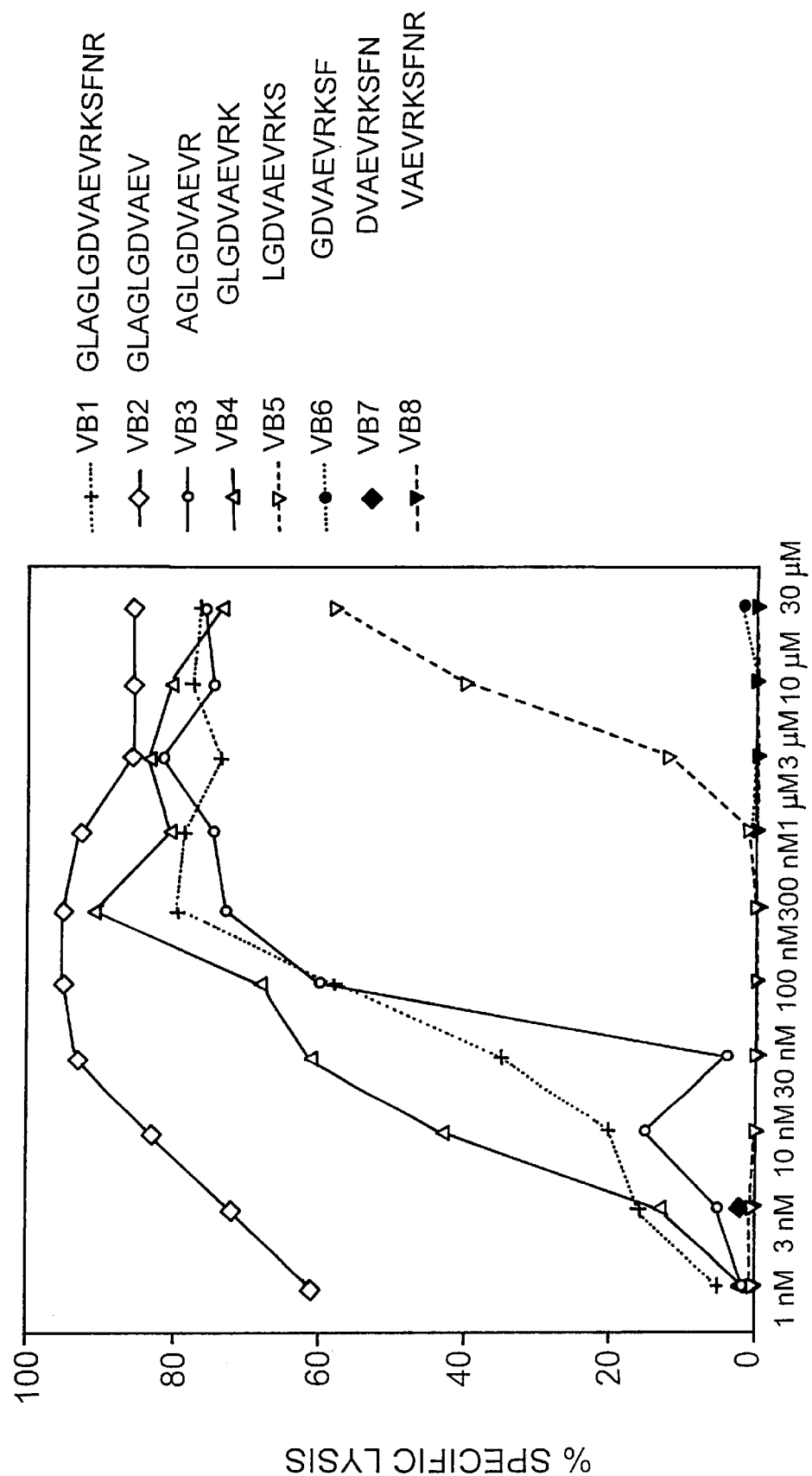
FIG. 1 CTL lysis of T2 cells pulsed with peptides derived from brain glycogen phosphorylase.

SEQ ID NO: 1 The shortest fragment of brain glycogen phosphorylase nucleic acid prepared by exonuclease III digestion which was able to confer expression of the antigen recognized by CTL 246/76.

SEQ ID NO:2 A fragment of brain glycogen phosphorylase nucleic acid ending at position 161.

SEQ ID NO:3 A fragment of brain glycogen phosphorylase nucleic acid ending at position 140.

SEQ ID NO:4. A 17 mer peptide (brain glycogen phosphorylase aa 18–33).

SEQ ID NO:5 An 11 mer peptide (aa 1–11) derived from SEQ ID NO:4.

SEQ ID NO:6 A 10 mer peptide (aa 3–12) derived from SEQ ID NO:4.

SEQ ID NO:7 A 10 mer peptide (aa 4–13) derived from SEQ ID NO:4.

SEQ ID NO:8 A 10 mer peptide (aa 5–14) derived from SEQ ID NO:4.

SEQ ID NO:9 A 10 mer peptide (aa 6–15) derived from SEQ ID NO:4.

SEQ ID NO:10 A 10 mer peptide (aa 7–16) derived from SEQ ID NO:4.

SEQ ID NO: 11 A 10 mer peptide (aa 8–17) derived from SEQ ID NO:4.

SEQ ID NO:12 A 10 mer peptide (aa 2–11) derived from SEQ ID NO:5.

SEQ ID NO: 13 A 9 mer peptide (aa 3–11 ) derived from SEQ ID NO:5.

SEQ ID NO:14 A 8 mer peptide (aa 4–11) derived from SEQ ID NO:5.

SEQ ID NO:15 A 7 mer peptide (aa 5–11) derived from SEQ ID NO:5.

SEQ ID NO:16 A 6 mer peptide (aa 6–11) derived from SEQ ID NO:5.

SEQ ID NO: 17 A sense primer for specific PCR amplification of brain glycogen phosphorylase.

SEQ ID NO: 18 An antisense primer for specific PCR amplification of brain glycogen phosphorylase.

SEQ ID NO: 19 An 11 mer peptide of the liver glycogen phosphorylase.

SEQ ID NO:20 An 11 mer peptide of the muscle glycogen phosphorylase.

SEQ ID NO:21 The full length sequence of the brain glycogen phosphorylase cDNA.

SEQ ID NO:22 The translation product of SEQ ID NO:21.

SEQ ID NO:23 The nucleic acid encoding SEQ ID NO:14.

SEQ ID NO:24 The nucleic acid encoding SEQ ID NO:13.

SEQ ID NO:25 The nucleic acid encoding SEQ ID NO:12.

DETAILED DESCRIPTION OF THE INVENTION

An antigen recognized on a melanoma by autologous CTL restricted by HLA-A2 is encoded by a previously known gene, brain glycogen phosphorylase. This gene is silent by PCR analysis in all normal tissues examined, except for brain and retinal pigment epithelium, and it is expressed in several tumor samples.

EXAMPLE 1
Description of an Anti-melanoma CTL Clone from Patient LB373

Tumor line LB373-MEL is a melanoma cell line derived from a tumor sample of a patient named LB373. A sample thereof was irradiated, so as to render it non-proliferative. These irradiated cells were then used to isolate cytolytic T cell clones ("CTLs") specific thereto.

A sample of peripheral blood lymphocytes ("PBLs") was taken from patient LB373, and contacted to the irradiated melanoma cells. After 14 days, the mixture was observed for lysis of the melanoma cells, which indicated that CTLs specific for a complex of peptide and HLA molecule presented by the carcinoma cells were present in the sample.

The lysis assay employed was a chromium release assay following Herin et al., Int. J. Cancer 39:390–396 (1987). The assay, however, is briefly described herein. The target melanoma cells were grown in vitro, and then resuspended at $10^7$ cells/ml in Dulbecco's Modified Eagles Medium (DMEM), supplemented with 30% FCS, and incubated for 45 minutes at 37° C. with 200 µCi/ml of Na($^{51}$Cr)O$_4$. Labeled cells were washed three times with DMEM. These were then resuspended in DMEM supplemented with 10 mM Hepes and 10% fetal calf serum (FCS), after which 100 µl aliquots containing $10^3$ cells were distributed into 96 well microplates. Samples of lymphocytes were added in 100 µl of the same medium, and assays were carried out in duplicate. Plates were centrifuged for 4 minutes at 100 g and incubated for four hours at 37° C. in a 8% CO$_2$ atmosphere.

Plates were centrifuged again, and 100 µl aliquots of supernatant were collected and counted. Percentage of $^{51}$Cr release was calculated as follows:

$$\%^{51}Cr \text{ release} = \frac{(ER-SR)}{(MR-SR)} \times 100$$

where ER is observed, experimental $^{51}$Cr release, SR is spontaneous release measured by incubating $10^3$ labeled cells in 200 µl of medium alone, and MR is maximum release, obtained by adding 100 µl 0.3% Triton X-100 to target cells.

Those mononuclear blood samples which showed high CTL activity were expanded and cloned via limiting dilution, and were screened again, using the same methodology. A first CTL clone was then isolated. The clone is referred to as 246/76 hereafter.

CTL clone 246/76 produced TNF when stimulated with the autologous tumor cells. Melanoma cell lines showing at least one class I molecule with the melanoma cell line LB373-MEL were tested for recognition by CTL clone 246/76. Cell lines sharing the HLA-A2 molecule were recognized by the CTL. The conclusion was that CTL 246/76 recognized an antigen presented by HLA-A2.

EXAMPLE 2
Isolation of a cDNA Clone that Directs the Expression of the Antigen Recognized by CTL 246/76

A. cDNA Library

RNA was isolated from LB373-MEL, and poly-A$^+$ RNA was purified by oligo-dT binding. cDNA was prepared by reverse transcription with an oligo-dT primer containing a Not I site, followed by second strand synthesis (Superscript Choice System, BRL, Life Technologies). The cDNA was then ligated to a BstXI adaptor, digested with NotI, size-fractionated (Sephacryl S-500 HR columns, BRL, Life Technologies) and cloned unidirectionally into the BstXI and NotI sites of pcDNA-I-Amp (Invitrogen). The recombinant plasmid was then electroporated into TOP10F' E. coli bacteria. 700 pools of 100 recombinant bacteria were amplified and plasmid DNA of each pool was extracted by alkaline lysis, potassium acetate precipitation and phenol extraction.

B. Transfection of Cells and Identification of cDNA

Most autologous CTL recognized COS cell transfected with HLA-A2 alone. Thus other cells were prepared to present the peptide recognized by CTL 246/76.

Two cell systems were used for isolation of cDNAs encoding the peptide recognized by CTL 246/76. HeLa cells expressing the BK virus large T antigen (hereinafter HOB cells) were able to present the peptide encoded by a control cDNA at a level similar to that observed for COS cells: a tyrosinase cDNA diluted in 200 unrelated cDNAs was recognized by anti-tyrosinase CTLs. The second cell system was purchased from Invitrogen (San Diego, Calif.). 293-EBNA-1 cells were able to present a peptide derived from tyrosinase cDNA cloned in pCEP4 even when diluted 1:800 with unrelated cDNAs. This second system was used to confirm the identity of the cDNA isolated using the HOB cell system.

The transfection of HOB cells was made in duplicate wells. Briefly, samples of HOB cells were seeded, at 15,000 cells/well into tissue culture flat bottom microwells, in DMEM supplemented with 10% fetal calf serum. The cells were incubated overnight at 37° C., medium was removed and then replaced by 100 µl/well total volume of DMEM medium containing 20% Nu-Serum (Collaborative Research, Bedford, Mass.), 300 µg/ml DEAE-dextran, and 200 µM chloroquine, plus 100 ng of the LB373-MEL cDNA library cloned in pcDNAI/Amp and 50 ng of HLA-A2 cloned in pcDNAI/Amp. Following four hours of incubation at 37° C., the medium was removed, and replaced by 50 μl of PBS containing 10% dimethyl sulfoxide (DMSO). This medium was removed after two minutes and replaced by 200 μl of DMEM supplemented with 10% FCS.

Following this change in medium, HOB cells were incubated for 48 hours at 37° C. The transfectants then were screened with CTL 246/76. After first removing the medium, 2000 CTL 246/76 cells were added to each well in 100 μl of medium containing 25 U/ml IL-2. The amount of TNF present in the supernatant was then measured by testing its cytotoxicity for WEHI 164.13 cells. Most pools gave a TNF concentration below 5 pg/ml. cDNAs from pools which gave higher concentrations in both of the duplicate wells were cloned in bacteria. Their plasmid DNA was extracted and transfected into HOB cells with HLA-A2. The transfectants were screened with CTL 246/76. One cDNA clone gave a high TNF production by CTL 246/76. The cDNA was sequenced, compared with DNA sequence databases and determined to encode brain glycogen phosphorylase.

EXAMPLE 3

Identification of the Portion of Brain Glycogen Phosphorylase Encoding a Tumor Rejection Antigen Fragments of the brain glycogen phosphorylase cDNA were prepared by exonuclease III digestion from the 3' end of the cDNA according to art standard procedures, were cloned into an expression vector and transfected into HOB cells with HLA-A2 as described above. As a positive control, the brain glycogen phosphorylase cDNA was cotransfected with HLA-A2 into HOB cells. These transfectants were used to provoke release of TNF from CTL 246/76 cells. The shortest fragment prepared by exonuclease III digestion which was able to confer expression of the antigen recognized by CTL 246/76 ended 100 bp after the start codon (SEQ ID NO: 1).

Shorter fragments were generated by PCR. A fragment ending at position 161 (SEQ ID NO:2) did confer expression of the antigen. A shorter fragment ending at position 140 (SEQ ID NO:3) did not confer expression of the antigen. Thus, at least the valine residue encoded at nucleotides 141, 142 and 143 of brain glycogen phosphorylase was important for efficient recognition of the brain glycogen phosphorylase tumor rejection antigen by CTL 246/76.

EXAMPLE 4

Identification of Brain Glycogen Phosphorylase Tumor Rejection Antigen Peptide

Synthetic peptides corresponding to the 3' end of SEQ ID NO:2 were synthesized and tested for lysis of HLA-A2 expressing cells. For these assays, T2 cells were used. T2 cells are HLA-A2+ cells which have an antigen-processing defect resulting in an increased capacity to present exogenous peptides. T2 cells were mixed with a synthetic peptide corresponding to a 3' portion of SEQ ID NO:3. CTL 246/76 cells were added and lysis was measured after 4 hours (FIG. 1). Peptide VB1 (GLAGLGDVAEVRKSFNR, SEQ ID NO:4) efficiently stimulated the lysis of T2 cells bearing HLA-A2. To determine the boundaries of the brain glycogen phosphorylase tumor rejection antigen, we tested a series of 10 mer and 11 mer peptides (SEQ ID NOs:5–11), i.e., peptides of 10 or 11 amino acids, derived from the 17 mer peptide (SEQ ID NO:4) previously used to stimulate lysis by CTL 246/76 cells (FIG. 1). One of these peptides (LGDVAEVRKS, SEQ ID NO:8) was recognized by CTL 246/76, but to a far lesser extent than the VB1 peptide (SEQ ID NO:4), which suggested that the nonamer (SEQ ID NO:8) was lacking an amino acid important for efficient recognition by CTL 246/76. The 10 mer peptide which includes the glycine immediately to the amino terminal side of SEQ ID NO: 8 (GLGDVAEVRK, SEQ ID NO:7) was efficiently recognized by CTL 246/76, as were the peptides of SEQ ID NO:5 and SEQ ID NO:9.

EXAMPLE 5

Activity of Brain Glycogen Phosphorylase Tumor Rejection Antigen Peptides

This example shows the ability of the brain glycogen phosphorylase TRA peptides to induce lysis of HLA-A2-expressing cells pulsed with such peptides and the relative efficiencies of the 6 mer, 7 mer, 8 mer, 9 mer, 10 mer and 11 mer peptides.

Figure 2A:
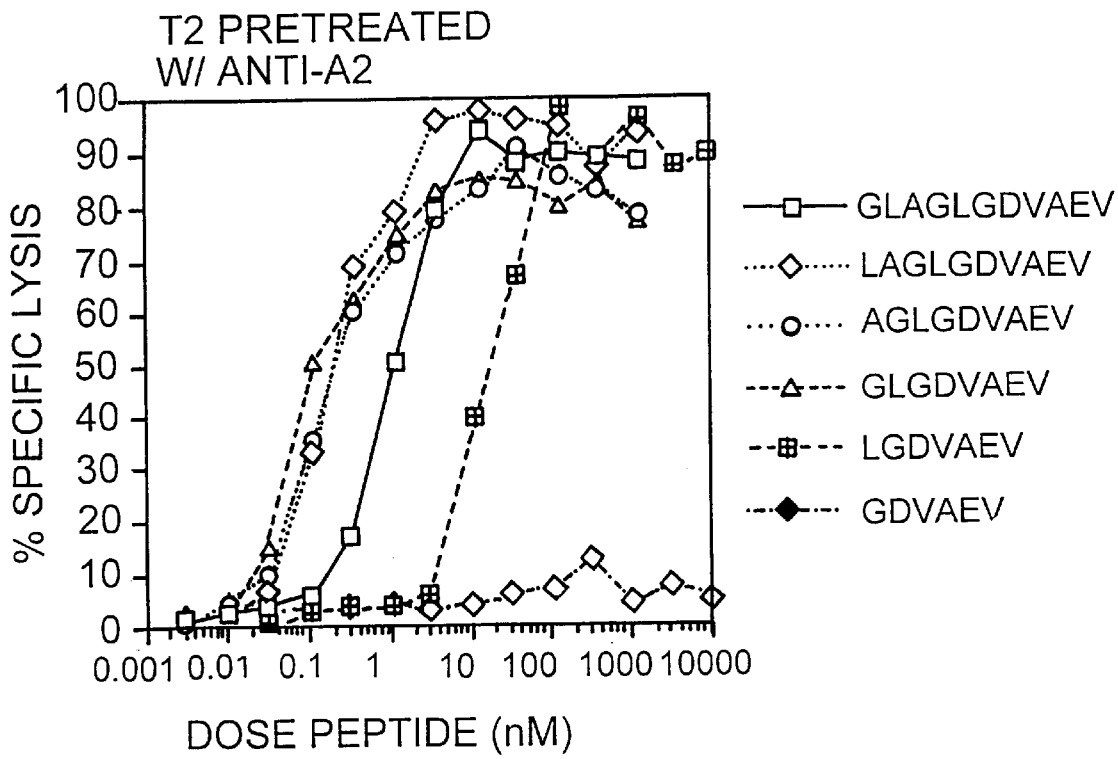
FIG. 2A depicts the results after pretreatment of T2 cells with anti-HLA-A2 antibody.
Figure 2B:
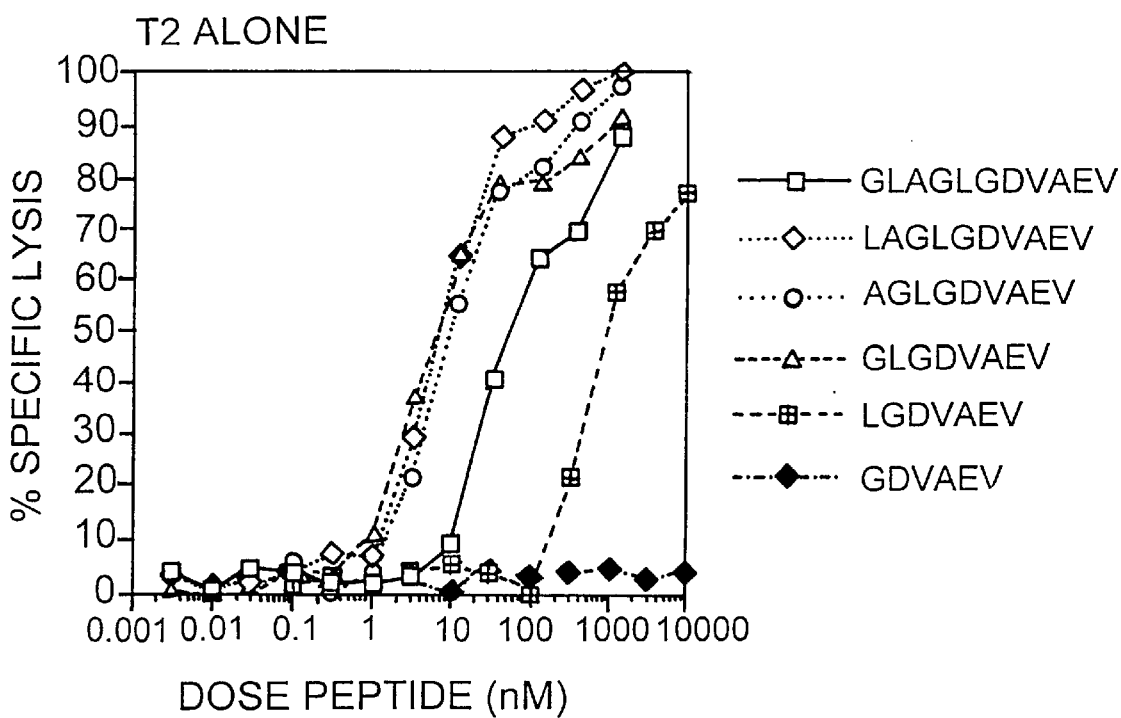
FIG. 2B depicts the result without pretreatment.

Brain glycogen phosphorylase peptides of decreasing size were synthesized based on the 11 mer peptide, VB2 (SEQ ID NO:5), by successively removing one amino acid from the amino terminal end of the peptide. These peptides, of 10, 9, 8, 7, and 6 amino acids, are represented as SEQ ID NOs: 12–16 respectively (see FIG. 2). These peptides were tested for the ability to induce cell lysis of HLA-A2+ T2 cells by CTL 246/76 cells in a dose response assay. Lyophilized peptides were dissolved at 20 mg/ml in DMSO, then diluted to 2 mg/ml in 10 mM acetic acid and stored at −80° C. Target cells, HLA-A2+ T2 cells, were labeled with $^{51}$Cr, as described above, for 1 hour at 37° C. followed by extensive washing to remove unincorporated label. T2 cells were pretreated (FIG. 2A) or not pretreated (FIG. 2B) with anti-HLA-A2 antibody, MA2.1 (Wölfel et al., European Journal of Immunology 24: 759–764, 1994), and then incubated in 96-well microplates in the presence of various concentrations of peptides for 30 minutes at 37° C. CTL 246/76 were then added in an equal volume of medium at an effector:target ratio of 30:1. Chromium-51 release was measured after 4 hours. FIG. 2 shows the results of the dose response assay. The 8 mer, 9 mer and 10 mer peptides (SEQ ID NOs:12–14) most efficiently stimulated the lysis of T2 cells bearing HLA-A2. The 11 mer peptide (VB1, SEQ ID NO:5) was about 1 log less active than the optimal peptides. The 7 mer peptide (SEQ ID NO: 15) was about 2 logs less active than the optimal peptides. The 6 mer peptide (SEQ ID NO: 16) exhibited little or no activity.

EXAMPLE 6

Expression of Brain Glycogen Phosphorylase Gene

The expression of brain glycogen phosphorylase was tested by PCR using the following primers:

SEQ ID NO:17— 5'- TGC CAG GCA CAG GTG GAC CA -3' (sense primer, nucleotides 2369–2388)

SEQ ID NO:18— 5'- CAG ACC CCA GAA TCC AGA GGC -3' (antisense primer, nucleotides 2890–2910)

First, total RNA was taken from the particular sample, using art recognized techniques. This RNA was used to prepare cDNA. The protocol used to make the cDNA involved combining 4 μl of 5× reverse transcriptase buffer, 1 μl of each dNTP (10 mM), 2 μl of dithiothreitol (100 mM), 2 μl of dT-15 primer (20 μM), 0.5 μl of RNasin (40 units/μl), and 1 μl of M-MLV reverse transcriptase (200 units/μl). Next, 6.5 μl of template RNA (1 μg/3.25 μl water, or 2 μg total template RNA) was added. The total volume of the mixture was 20 μl. This was mixed and incubated at 42° C. for 60 minutes, after which it was chilled on ice. A total of 80 μl of water was then added, to 100 μl total. This mixture was stored at −20° C. until used in PCR.

The reagents for PCR included:

5 microliters of 10× DynaZyme buffer 20 pmoles of each primer 5 nanomoles of each dNTP 1 unit of polymerizing enzyme "Dynazyme" (2 units/μl)

5 μl of cDNA (corresponding to 100 ng total RNA)

water to a final volume of 50 μl

The mixture was combined, and layered with one drop of mineral oil. The mixture was transferred to a thermocycler block, preheated to 94° C., and amplification was carried out for one cycle of 15 min at 94° C., followed by 25 cycles of:

1 min. at 94° C.

30 sec. at 65° C.

2 min. at 72° C.

A final extension step of 15 min. was then performed at 72° C. The PCR product was visualized on an agarose gel (1.5%) containing ethidium bromide.

Figure 3A:
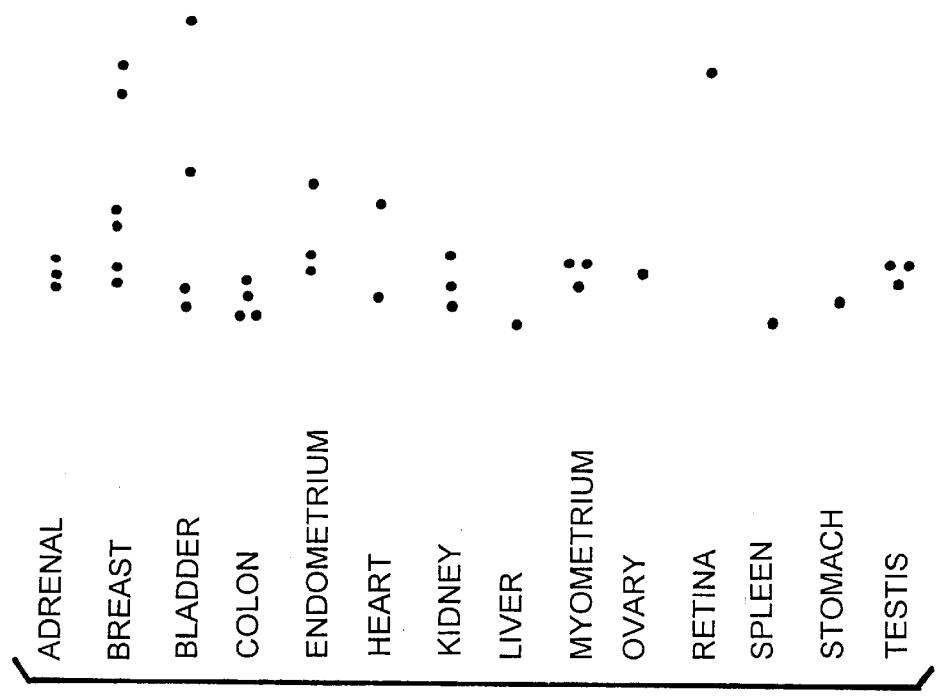
FIG. 3 Expression of brain glycogen phosphorylase in normal (FIG. 3A) and tumor tissues (FIG. 3B).
Figure 3B:
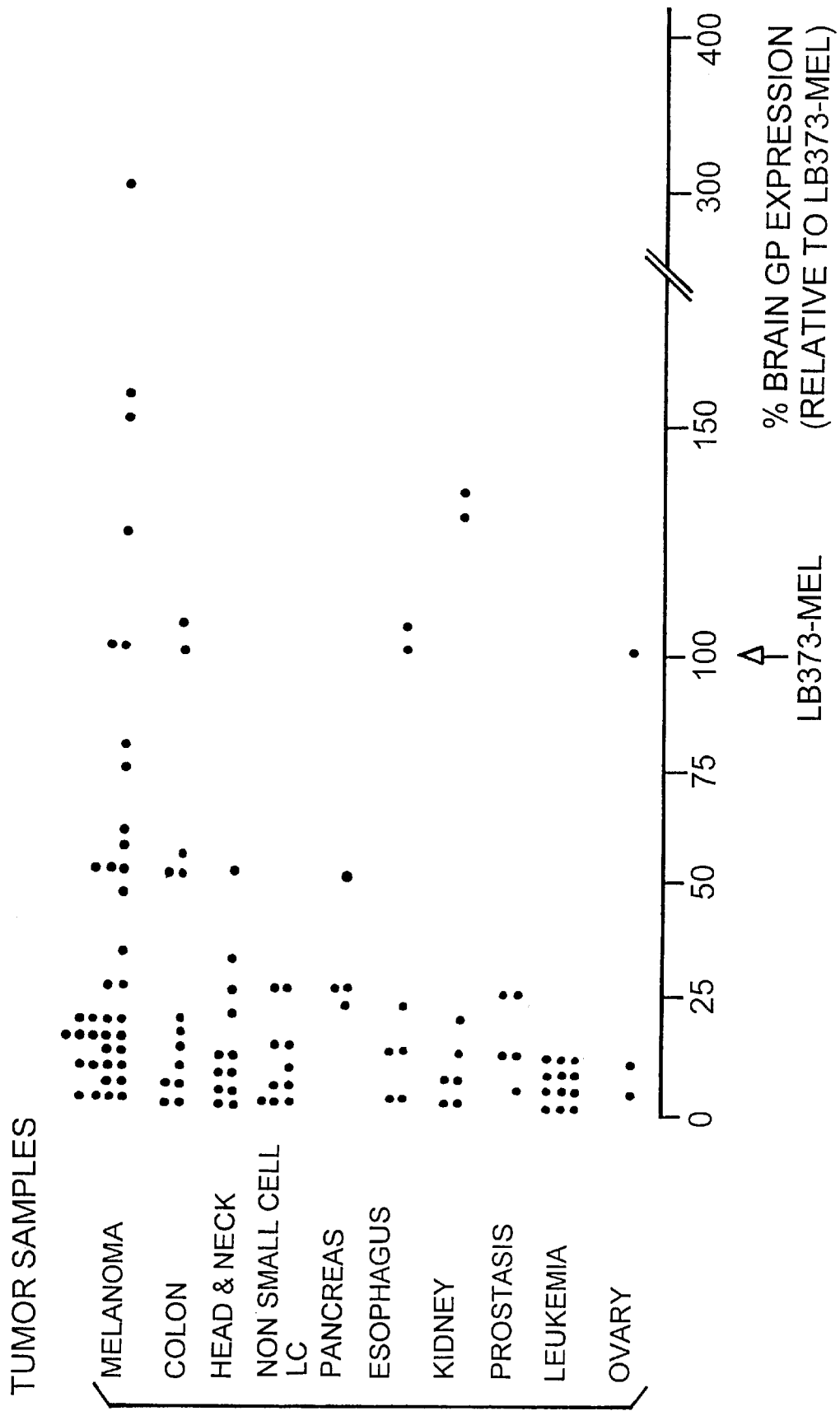

The brain glycogen phosphorylase gene demonstrated a pattern of over-expression in tumors. The gene was expressed at levels lower that the level of expression found in LB373-MEL cells in all normal tissues tested (FIG. 3). In particular, the gene was expressed weakly in normal adrenals, bladder, breast, colon, endometrium, heart, kidney, liver, myometrium, ovary, retina, spleen, stomach, and testis. The gene, however, was found to be expressed in a variety of tumor tissue samples (FIG. 3). A 10- to 40-fold greater expression of brain glycogen phosphorylase was observed in 15% of melanomas and a similar proportion of colon, ovarian and renal carcinomas. These results were confirmed by staining tumor samples with an antiserum specific for the brain glycogen phosphorylase (Ignacio et al., Brain Res. 529: 42–49, 1990): tumor tissue demonstrated a high level of staining but the surrounding normal tissue was negative for staining.

EXAMPLE 7

Homologous Peptides of Liver and Muscle Isoforms are not Recognized by CTL 246/76

Figure 4:
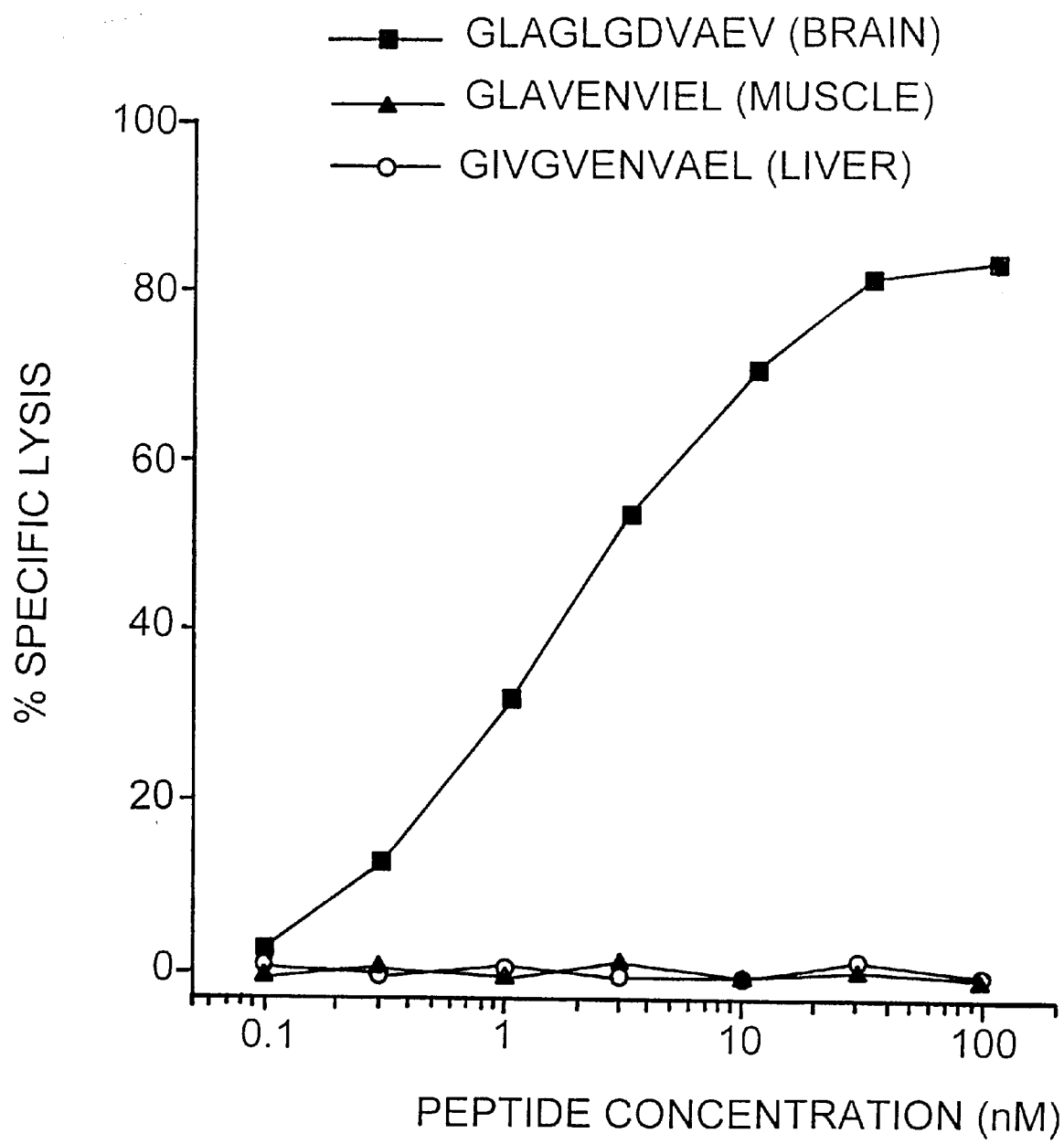
FIG. 4 CTL lysis of T2 cells pulsed with homologous peptides derived from brain, muscle and liver glycogen phosphorylase isoforms.

The muscle, liver and brain isoforms of glycogen phosphorylase display about an 80% amino acid identity (Newgard et al., J. Biol. Chem. 263: 3850–3857, 1988). To demonstrate that the tumor rejection antigen was specific for the brain isoform, 11 mer peptides of the liver (GIVGVENVAEL, SEQ ID NO:19) and muscle (GLAGVENVIEL, SEQ ID NO:20) isoforms were synthesized and used in a dose response-chromium release assay as described above in Example 5. As shown in FIG. 4, the liver and muscle peptides do not provoke lysis, whereas the brain peptide, VB1 (SEQ ID NO:5), induces specific lysis.

EXAMPLE 8

Normal Cells are not Lysed by CTL246/76

This example describes CTL lysis experiments with various cell lines with or without incubation with the peptide of SEQ ID NO:14. LB373-MEL cells, normal B cells from patient LB373 transformed with EBV (LB373-EBV) and normal peripheral blood lymphocytes from the same patient (LB373-PBL) were tested for lysis by CTL 246/76 cells in a dose response assay. These cells were incubated with CTL246/76 at the effector/target ratios shown in FIG. 5A and assayed for lysis as described above. Only the LB373-MEL cells were lysed by the CTL246/76, demonstrating that LB373-EBV and LB373-PBL cells were not recognized by the CTL because such cells do not normally express the brain glycogen phosphorylase tumor rejection antigen.

Figure 5:
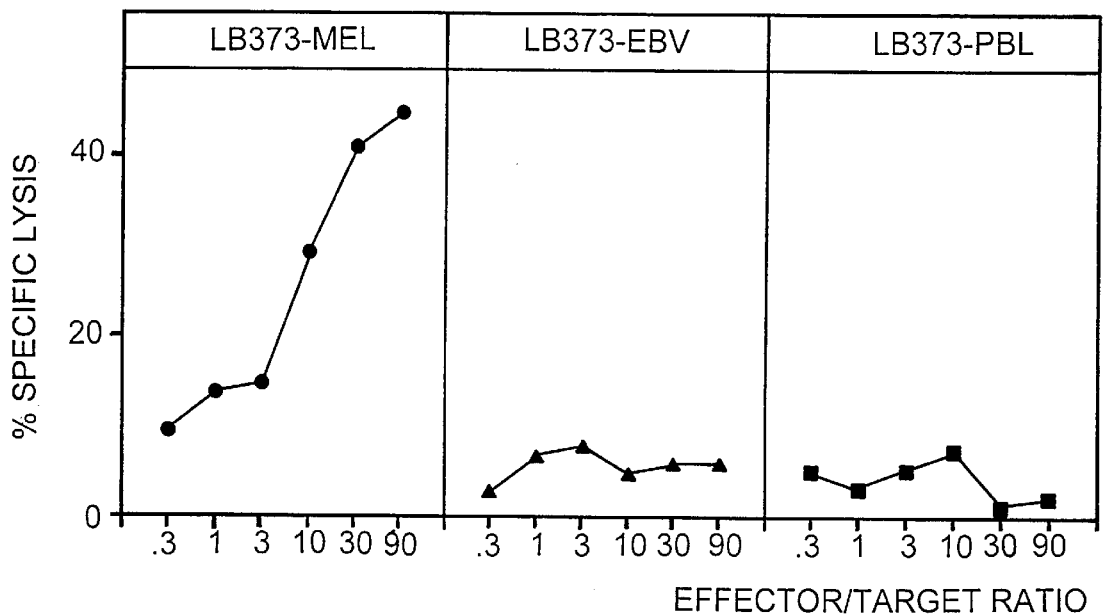
FIG. 5 CTL lysis experiments with various cell lines pulsed with the peptide of SEQ ID NO: 14.
Figure 5:
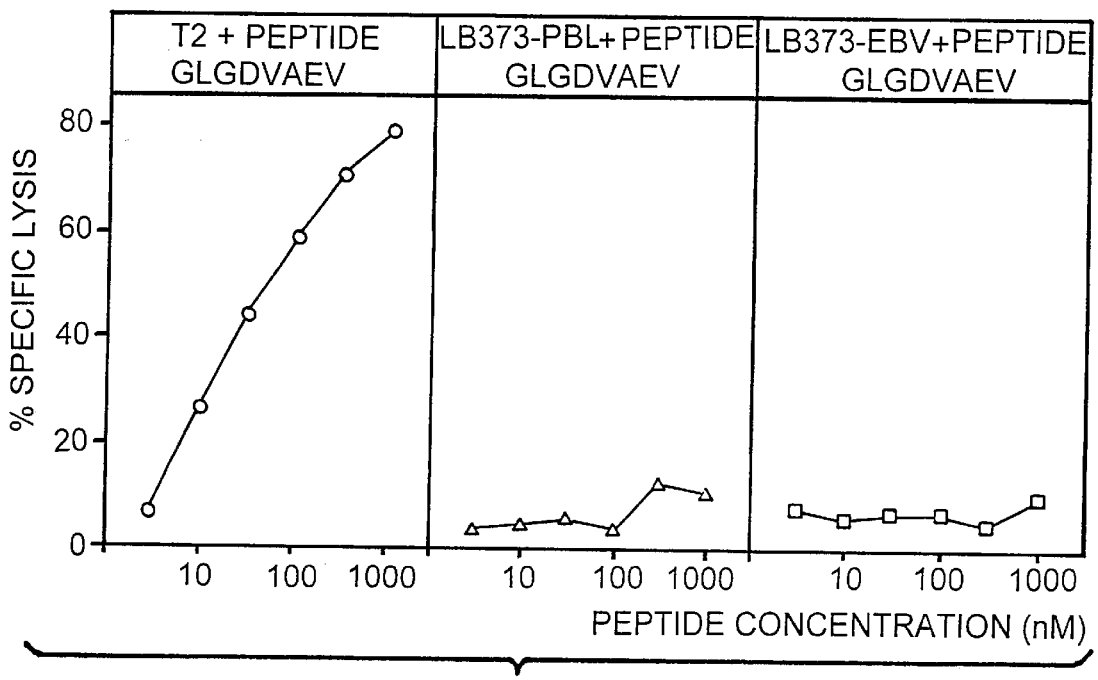

It was next determined whether these cells would be lysed by CTL if pulsed with a brain glycogen phosphorylase peptide. The peptide of SEQ ID NO: 14 was tested for the ability to induce cell lysis of LB373-MEL cells, LB373-EBV cells, and HLA-A2$^+$ T2 cells by CTL 246/76 cells in a dose response assay as in previous examples. FIG. 5B shows the results of the dose response assay. LB373-EBV and LB373-PBL were not lysed by CTL 246/76, but a non-autologous cell line, T2, was lysed by CTL 246/76.

The invention pertains to the abnormal expression of human brain glycogen phosphorylase. A gene encoding human brain glycogen phosphorylase is presented in SEQ ID NO:21. Alleles are also a part of the invention. Alleles share >95% homology with SEQ ID NO:21 and code for a brain glycogen phosphorylase tumor rejection antigen precursor. They hybridize to a nucleic acid molecule consisting of SEQ ID NO:21, under stringent conditions. The term "stringent conditions" as used herein refers to parameters with which the art is familiar. More specifically, stringent conditions, as used herein, refers to hybridization at 65° C. in hybridization buffer (3.5× SSC, 0.02% Ficoll, 0.02% Polyvinyl pyrolidone, 0.02% Bovine Serum Albumin, 25 mM NaH$_2$PO$_4$ (pH 7), 0.5% SDS, 2 mM EDTA). SSC is 0.15M Sodium Chloride/0.15M Sodium Citrate, pH 7; SDS is Sodium Dodecyl Sulfate; and EDTA is ethylenediaminetetraacetic acid. After hybridization, the membrane upon which the DNA is transferred is washed at 2× SSC at room temperature and then at 0.1× SSC/0.1× SDS at 65° C.

There are other conditions, reagents, and so forth which can be used, which result in the same degree of stringency. The skilled artisan will be familiar with such conditions, and thus they are not given here. The skilled artisan also is familiar with the methodology for screening cells, preferably cancer cells, for expression of such molecules which then are routinely isolated, followed by isolation of the pertinent nucleic acid.

Abnormal expression of brain glycogen phosphorylase can be detected by a variety of technologies. For example, antibodies specific for brain glycogen phosphorylase have been described in the literature and can be prepared by routine procedures, some of which are described in greater detail below. More preferably, expression (and relative expression levels in various tissues) can be detected by measuring mRNA. For example, the expression of brain glycogen phosphorylase in tumor cells or tissues can be compared to control cells or tissues of like origin. PCR and other techniques can be used for this purpose. For any pair of PCR primers constructed and arranged to selectively amplify the brain glycogen phosphorylase gene, a brain glycogen phosphorylase specific primer may be used. Such a specific primer would fully hybridize to a contiguous stretch of nucleotides only in brain glycogen phosphorylase, but would hybridize only in part to non-brain glycogen phosphorylase genes. For efficient PCR priming and brain glycogen phosphorylase identification, the brain glycogen phosphorylase specific primer should be constructed and arranged so it does not hybridize efficiently at its 3' end to glycogen phosphorylase genes other than brain glycogen phosphorylase. The mismatch generated at the 3' end of the primer when hybridized to glycogen phosphorylase genes, other than brain glycogen phosphorylase, would preclude efficient amplification of those genes. Primers can be chosen by one of ordinary skill in the art based on the published sequences of the brain, liver and muscle isoforms of glycogen phosphorylase (see, e.g. Newgard et al., J. Biol. Chem. 263: 3850–3857, 1988). Additional methods which can distinguish nucleotide sequences of substantial homology, such as ligase chain reaction ("LCR") and other methods, will be apparent to skilled artisans.

The invention also includes the use of nucleic acid sequences which include alternative codons that encode the same amino acid residues as encoded by the brain glycogen phosphorylase genes. For example, as disclosed above in Example 5, a decameric peptide LAGLGDVAEV (SEQ ID NO: 12) is a brain glycogen phosphorylase tumor rejection antigen. The leucine residues (amino acids No. 1 and 4 of SEQ ID NO: 12) for example, are encoded by the codons CTG and CTA, respectively. In addition to CTG and CTA, leucine amino acid residues may also be encoded by the codons CTC, CTT, TTA and TTG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising a brain glycogen phosphorylase tumor rejection antigen include: CGA, CGC, CGG, CGT, AGA and AGG (arginine codons); GGA, GGC, GGG, and GGT (glycine codons); GCA, GCC, GCG, and GCT (alanine codons); GAC and GAU (aspartic acid codons); and CGA, CGC, CGG, CGT, AGA, and AGG (arginine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The examples above also show the isolation of peptides which are brain glycogen phosphorylase TRAs. These exemplary peptides are processed translation products of the nucleic acids of brain glycogen phosphorylase (SEQ ID NO:21). As such, it will be appreciated by one of ordinary skill in the art that the translation products from which a brain glycogen phosphorylase TRA is processed to a final form for presentation may be of any length or sequence so long as they encompass the "core" brain glycogen phosphorylase TRA represented by SEQ ID NO:15. As demonstrated in the examples above, peptides or proteins as small as 7, 8, 9, 10, or 11 amino acids and as large as the amino acid sequence encoded by the brain glycogen phosphorylase cDNA are appropriately processed if necessary, presented by HLA-A2 and recognized by CTL246/76. The peptide of SEQ ID NO:15 may have one, two, three, four, five, six, seven, eight, nine, ten, or more amino acids added to either or both ends. Thus the tumor rejection antigen can consist essentially of seven consecutive amino acids of SEQ ID NO:22 inclusive of SEQ ID NO: 15, eight consecutive amino acids of SEQ ID NO:22 inclusive of SEQ ID NO: 15, nine consecutive amino acids of SEQ ID NO:22 inclusive of SEQ ID NO: 15, ten consecutive amino acids of SEQ ID NO:22 inclusive of SEQ ID NO:15, eleven consecutive amino acids of SEQ ID NO:22 inclusive of SEQ ID NO: 15, twelve consecutive amino acids of SEQ ID NO:22 inclusive of SEQ ID NO:15, thirteen consecutive amino acids of SEQ ID NO:22 inclusive of SEQ ID NO:15, fourteen consecutive amino acids of SEQ ID NO:22 inclusive of SEQ ID NO: 15, fifteen consecutive amino acids of SEQ ID NO:22 inclusive of SEQ ID NO: 15, sixteen consecutive amino acids of SEQ ID NO:22 inclusive of SEQ ID NO: 15, seventeen consecutive amino acids of SEQ ID NO:22 inclusive of SEQ ID NO:15, eighteen consecutive amino acids of SEQ ID NO:22 inclusive of SEQ ID NO:15, nineteen consecutive amino acids of SEQ ID NO:22 inclusive of SEQ ID NO:15, and/or up to 100 consecutive amino acids of SEQ ID NO:22 inclusive of SEQ ID NO:15 (i.e., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 consecutive amino acids). The antigenic portion of such peptides is cleaved out under physiological conditions for presentation by HLA class I molecules.

The amino acid sequence of proteins and peptides from which brain glycogen phosphorylase TRAs are derived may be of natural or non-natural origin, that is, they may comprise a natural brain glycogen phosphorylase TRAP molecule or may comprise a modified sequence as long as the amino acid sequence retains the tumor rejection antigen sequence recognized by the CTL when presented on the surface of a cell. For example, brain glycogen phosphorylase tumor rejection antigens in this context may be fusion proteins of a brain glycogen phosphorylase tumor rejection antigen and unrelated amino acid sequences, synthetic peptides of amino acid sequences shown in SEQ ID NO: 15, SEQ ID NO: 14, SEQ ID NO: 13, SEQ ID NO:12 or SEQ ID NO:5, labeled peptides, peptides isolated from patients with melanoma, peptides isolated from cultured cells which express brain glycogen phosphorylase, peptides coupled to nonpeptide molecules, for example, in certain drug delivery systems, and other molecules which include the amino acid sequence of SEQ ID NO: 15.

It will also be seen from the examples that the invention embraces the use of the sequences in expression vectors, as well as to transfect host cells and cell lines, be these prokaryotic (e.g., *E. coli*), or eukaryotic (e.g., CHO cells, COS cells, HeLa cells, yeast expression systems and recombinant baculovirus expression in insect cells). The expression vectors require that the pertinent sequence, i.e., those described supra, be operably linked to a promoter. As it has been found that human HLA-A2 presents a TRA derived from these genes, the expression vector may also include a nucleic acid sequence coding for an HLA molecule, especially HLA-A2. In a situation where the vector contains both coding sequences, it can be used to transfect a cell which does not normally express either one. The TRAP or TRA coding sequence may be used alone, when, e.g. the host cell already expresses HLA-A2. Of course, there is no limit on the particular host cell which can be used. As the vectors which contain the two coding sequences may be used in HLA-A2 presenting cells if desired, and the nucleic acid coding for the TRAP or TRA can be used in host cells which do not express HLA-A2.

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-A2. In the former situation, such determinations can be carried out via any standard nucleic acid determination assay, including the polymerase chain reaction, or assaying with labeled hybridization probes. In the latter situation, assaying with binding partners for complexes of TRA and HLA, such as antibodies, is especially preferred. An alternate method for determination is a TNF release assay, of the type described supra.

Other TRAPs or TRAs encoded by brain glycogen phosphorylase and recognized by other CTL clones and/or presented by other HLA molecules may be isolated by the procedures detailed herein. (There are numerous HLA molecules known to those skilled in the art, including but not limited to, those encoded by HLA-A, HLA-B, HLA-C, HLA-E, HLA-F and HLA-G genes.) A variety of methodologies well-known to the skilled practitioner can be utilized to obtain isolated TRAP molecules, and/or TRAs derived therefrom. The protein may be purified from cells which naturally produce the protein. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce protein. Peptides comprising TRAs of the invention may also be synthesized in vitro. Those skilled in the art also can readily follow known methods for isolating proteins in order to obtain isolated TRAP and/or TRAs derived therefrom. These include, but are not limited to, immunochromatography, HPLC, size-exclusion chromatography, ion-exchange chromatography and immune-affinity chromatography. These isolated molecules when processed and presented as the TRA, or as complexes of TRA and HLA, such as HLA-A2, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection. Vaccines also encompass naked DNA or RNA, encoding a brain glycogen phosphorylase TRA or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (Science 259:1745–1748, 1993).

The TRAP molecule, its associated TRAs, as well as complexes of TRA and HLA, may be used to produce antibodies, using standard techniques well known to the art. Standard reference works setting forth the general principles of antibody production include Catty, D., *Antibodies. A Practical Approach,* Vol. 1, IRL Press, Washington DC (1988); Klein, J., *Immunology: The Science of Cell-Non-Cell Discrimination,* John Wiley and Sons, New York (1982); Kennett, R., et al., *Monoclonal Antibodies, Hybridoma, A New Dimension In Biological Analyses,* Plenum Press, New York (1980); Campbell, A., *Monoclonal Antibody Technology,* in *Laboratory Techniques and Biochemistry and Molecular Biology,* Vol. 13 (Burdon, R. et al. EDS.), Elsevier Amsterdam (1984); and Eisen, H. N., *Microbiology,* third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the TRA/HLA complexes described herein.

When "disorder" is used herein, it refers to any pathological condition where the tumor rejection antigen precursor is expressed. An example of such a disorder is cancer, melanoma in particular.

Some therapeutic approaches based upon the disclosure are premised on a response by a subject's immune system, leading to lysis of TRA presenting cells, such as HLA-A2 cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant, such as a HeLa cell of the type described supra. These transfectants present the desired complex at their surface and, when combined with a CTL of interest, stimulate its proliferation. HeLa cells, such as those used herein, are widely available, as are other suitable host cells. Specific production of a CTL clone has been described above. The clonally expanded autologous CTLs then are administered to the subject. Other CTLs specific to brain glycogen phosphorylase may be isolated and administered by similar methods.

To detail a therapeutic methodology, referred to as adoptive transfer (Greenberg, J. Immunol. 136(5): 1917 (1986); Riddel et al., Science 257: 238 (7–10–92); Lynch et al, Eur. J. Immunol. 21: 1403–1410 (1991); Kast et al., Cell 59: 603–614 (11–17–89)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a brain glycogen phosphorylase sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a brain glycogen phosphorylase derived TRA is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated tumor cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. For example, nucleic acids which encode a brain glycogen phosphorylase TRA may be operably linked to promoter and enhancer sequences which direct expression of the brain glycogen phosphorylase TRA in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding brain glycogen phosphorylase TRAs. Nucleic acids encoding a brain glycogen phosphorylase TRA also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials de facto "infect" host cells. The cells which result present the complex of interest, and are recognized by autologous CTLs, which then proliferate.

A similar effect can be achieved by combining the TRAP or a stimulatory fragment thereof with an adjuvant to facilitate incorporation into HLA-A2 presenting cells in vivo. The TRAP is processed to yield the peptide partner of the HLA molecule while the TRA is presented without the need for further processing. Generally, subjects can receive an intradermal injection of an effective amount of the brain glycogen phosphorylase TRAP, and/or TRAs derived therefrom. Initial doses can be followed by booster doses, following immunization protocols standard in the art.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (Science 268: 1432–1434, 1995).

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. This can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated polypeptide fragment of the brain glycogen phosphorylase of SEQ ID NO: 22 wherein the fragment consists of at least the amino acid sequence of SEQ ID NO: 15 but not more than 75% of SEQ ID NO: 22.

2. The isolated polypeptide of claim 1 wherein the polypeptide is between 7 and 100 amino acids.

3. The isolated polypeptide of claim 2 wherein the amino acid sequence of SEQ ID NO: 15 has 1–10 amino acids of SEQ ID NO: 22 contiguous with SEQ ID NO: 15 added on either or both of the N- and C-termini.

4. The isolated polypeptide of claim 2 wherein the fragment consists of at least an amino acid sequence selected from the group consisting of SEQ ID NOS: 14, 13, 12, and 5.

5. The isolated polypeptide of claim 1 wherein the amino acid sequence of SEQ ID NO: 15 has 1–10 amino acids of SEQ ID NO: 22 contiguous with SEQ ID NO: 15 added on either or both of the N- and C-termini.

6. The isolated polypeptide of claim 1 wherein the fragment consists of at least an amino acid sequence selected from the group consisting of SEQ ID NOS: 14, 13, 12, and 5.

7. An isolated polypeptide selected from the group consisting of SEQ ID NOS: 15, 14, 13, 12, and 5.

8. An isolated polypeptide of claim 7 which is SEQ ID NO: 15.

9. An isolated polypeptide of claim 7 which is SEQ ID NO: 14.

10. An isolated polypeptide of claim 7 which is SEQ ID NO: 13.

11. An isolated polypeptide of claim 7 which is SEQ ID NO: 12.

12. An isolated polypeptide of claim 7 which is SEQ ID NO: 5.

13. An isolated polypeptide fragment of the brain glycogen phosphorylase of SEQ ID NO: 22 wherein the fragment consists of SEQ ID NO: 15 having 1–10 amino acids of SEQ ID NO: 22 contiguous with SEQ ID NO: 15 added on either or both of the N- and C-termini.

14. An isolated nucleic acid consisting of a sequence encoding the polypeptide fragment of any one of claims 2–4 and 7–13.

15. An expression vector wherein the isolated nucleic acid of claim 14 is operably linked to a promoter.

16. The expression vector of claim 15 which additionally contains a nucleic acid which codes for HLA-A2.

17. An isolated host cell transfected or transformed with the isolated nucleic acid of claim 14.

18. A method for preparing a polypeptide comprising culturing the isolated host cell of claim 17 under conditions which permit expression of the polypeptide and isolating the polypeptide from the culture.

19. The isolated polypeptide fragment of any one of claims 7–13 which is fused to a heterologous protein.

20. An isolated nucleic acid consisting of a sequence encoding the polypeptide fragment of claim 19.

21. An expression vector wherein the isolated nucleic acid of claim 20 is operably linked to a promoter.

22. The expression vector of claim 21 which additionally contains a nucleic acid which codes for HLA-A2.

23. An isolated host cell transfected or transformed with the isolated nucleic acid of claim 20.

24. A method for preparing a polypeptide comprising culturing the isolated host cell of claim 23 under conditions which permit expression of the polypeptide and isolating the polypeptide from the culture.

* * * * *